United States Patent
Robbins et al.

(10) Patent No.: US 11,083,773 B2
(45) Date of Patent: *Aug. 10, 2021

(54) PEPTIDES THAT BLOCK LEUKOCYTE RECRUITMENT AND METHODS OF USE

(71) Applicant: ARCH CANCER THERAPEUTICS, INC., Calgary (CA)

(72) Inventors: Stephen Mark Robbins, Calgary (CA); Donna Lorraine Senger, Calgary (CA); Jennifer Joy Rahn, Calgary (CA); Paul Kubes, Cochrane (CA)

(73) Assignee: ARCH CANCER THERAPEUTICS, INC., Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/129,942

(22) Filed: Sep. 13, 2018

(65) Prior Publication Data

US 2020/0038473 A1 Feb. 6, 2020

Related U.S. Application Data

(63) Continuation of application No. 15/893,252, filed on Feb. 9, 2018, now abandoned, which is a continuation of application No. 15/632,763, filed on Jun. 26, 2017, now abandoned, which is a continuation of application No. 15/253,048, filed on Aug. 31, 2016, now abandoned, which is a continuation of application No. 14/622,177, filed on Feb. 13, 2015, now Pat. No. 9,464,114.

(60) Provisional application No. 61/939,561, filed on Feb. 13, 2014.

(51) Int. Cl.
*A61K 38/10* (2006.01)
*G01N 33/50* (2006.01)
*C07K 7/08* (2006.01)
*A61K 38/00* (2006.01)

(52) U.S. Cl.
CPC ........... *A61K 38/10* (2013.01); *C07K 7/08* (2013.01); *G01N 33/5011* (2013.01); *G01N 33/5047* (2013.01); *A61K 38/00* (2013.01); *G01N 2800/26* (2013.01)

(58) Field of Classification Search
CPC ......... A61K 38/00; A61K 38/10; A61P 31/00; A61P 31/04; A61P 31/10; A61P 31/12; A61P 33/00; A61P 35/00; A61P 35/04; A61P 37/02; C07K 7/08; G01N 2800/26; G01N 33/5011; G01N 33/5047
See application file for complete search history.

(56) References Cited

U.S. PATENT DOCUMENTS

| | | |
|---|---|---|
| 4,244,946 A | 1/1981 | Rivier |
| 4,305,872 A | 12/1981 | Johnston |
| 4,316,891 A | 2/1982 | Guillemin |
| 5,223,409 A | 6/1993 | Ladner |
| 5,403,484 A | 4/1995 | Ladner |
| 5,571,698 A | 11/1996 | Ladner |
| 5,629,179 A | 5/1997 | Mierendorf |
| 5,766,905 A | 6/1998 | Studier |
| 2010/0324469 A1 | 12/2010 | Mori et al. |
| 2012/0023611 A1* | 1/2012 | Cao ............... C12N 15/8247 800/275 |

FOREIGN PATENT DOCUMENTS

| | | |
|---|---|---|
| WO | WO 2007/146188 | 12/2007 |
| WO | WO 2011/119484 | 12/2010 |

OTHER PUBLICATIONS

Fauchere et al., Infect. lmmun. 54:283-287 (1986).
Evans et al., J. Med. Chem. 30: 1229-1239 ( 1987).
Spatola et al. Life Sci. 38: 1243-1249 (1986).
Vale et al., Science 213:1394-1397 (1981).
Paget S (1989) The distribution of secondary growths in cancer of the breast. 1889. Cancer Metastasis Rev 8(2):98-101.
Chiang AC & Massague J (2008) Molecular basis of metastasis. N Engl J Med 359(26):2814-2823.
Nguyen DX, Bos PD, & Massague J (2009) Metastasis: from dissemination to organ-specific colonization. Nat Rev Cancer 9(4 ):27 4-284.
Bakalian S, Marshall JC, Logan P, Faingold D, Maloney S, Di Cesare S, Martins C, Femandes BF, & Bumier MN, Jr. (2008) Molecular pathways mediating liver metastasis in patients with uveal melanoma. Clin Cancer Res 14(4):951-956.
Sato T (2010) Locoregional management of hepatic metastasis from primary uveal melanoma. Semin Onco/ 37(2):127-138.
Scharffetter-Kochanek K, Lu H, Norman K, van Nood N, Munoz F, Grabbe S, McArthur M, Lorenzo I, Kaplan S, Ley K, Smith CW, Montgomery CA, Rich S, & Beaudet AL (1998) Spontaneous skin ulcera-tion and defective T cell function in CD18 null mice. J Exp Med 188(1 ):119-131.
Hess KR, Varadhachary GR, Taylor SH, Wei W, Raber MN, Lenzi R, & Abbruzzese JL. (2006) Metastatic patterns in adenocarcinoma. Cancer 106(7):1624-1633.
Jones S, Chen WO, Parmigiani G, Diehl F, Beerenwinkel N, Antal T, Traulsen A, Nowak MA, Siegel C, Velculescu VE, Kinzler KW, Vogelstein B, Willis J, & Markowitz SD (2008) Comparative lesion sequencing provides insights into tumor evolution. Proc Natl Acad Sci US A 105(11 ):4283-4288.
Roberge D, Hickeson M, Charest M, & Turcotte RE (2010) Initial McGill experience with fluorodeoxy-glucose pet/ct staging of soft-tissue sarcoma. Cliff Onco/ 17(6):18-22.

(Continued)

*Primary Examiner* — James H Alstrum-Acevedo
*Assistant Examiner* — Erinne R Dabkowski
(74) *Attorney, Agent, or Firm* — King & Spalding

(57) ABSTRACT

Disclosed are novel peptides comprising SEQ ID NO: 1 and modifications thereof, which are effective in blocking leukocyte recruitment. The disclosed peptides are useful for treating diseases associated with leukocyte recruitment for example inhibiting metastasis of a solid tumor to the liver and lungs and for treating sepsis. Also disclosed are methods of screening for compounds having the ability to block leukocyte recruitment.

4 Claims, 21 Drawing Sheets

Specification includes a Sequence Listing.

(56) References Cited

OTHER PUBLICATIONS

Du YC, Chou CK, Klimstra OS, & Varmus H (2011) Receptor for hyaluronan-mediated motility isoform B promotes liver metastasis in a mouse model of multistep tumorigenesis and a tail vein assay for metastasis. Proc Natl Acad Sci U SA 108(40):16753-16758.

Bemmo A, Dias C, Rose AA, Russo C, Siegel P, & Majewski J (2010) Exon-level transcriptome profiling in murine breast cancer reveals splicing changes specific to tumors with different metastatic abilities. PLoS One 5(8):e11981.

Tabaries S, Dong Z, Annis MG, Omeroglu A, Pepin F, Ouellet V, Russo C, Hassanain M, Metrakos P, Diaz Z, Basik M, Bertos N, Park M, Guettier C, Adam R, Hallett M, & Siegel PM (2011) Claudin-2 is selectively enriched in and promotes the formation of breast cancer liver metastases through engagement of integrin complexes. Oncogene 30(11):1318-1328.

Tabaries S, Dupuy F, Dong Z, Monast A, Annis MG, Spicer J, Ferri LE, Omeroglu A, Basik M, Amir E, Clemons M, & Siegel PM (2012) Claudin-2 promotes breast cancer liver metastasis by facilitating tumor cell interactions with hepatocytes. Mo/ Cell Biol.

Kang Y, Siegel PM, Shu W, Drobnjak M, Kakonen SM, Cordon-Cardo C, Guise TA, & Massague J (2003) A multigenic program mediating breast cancer metastasis to bone. Cancer Ce// 3(6):537-549.

Minn AJ, Gupta GP, Siegel PM, Bos PD, Shu W, Giri DD, Viale A, Olshen AB, Gerald WL, & Massague J (2005) Genes that mediate breast cancer metastasis to lung. Nature 436(7050):518-524.

Bos PD, Zhang XH, Nadal C, Shu W, Gomis RR, Nguyen DX, Minn AJ, van de Vijver MJ, Gerald WI., Foekens JA, & Massague J (2009) Genes that mediate breast cancer metastasis to the brain. Nature 459(7249):1005-1009.

Landemaine T, Jackson A, Bellahcene A, Rucci N, Sin S, Abad BM, Sierra A, Boudinet A, Guinebretiere JM, Ricevuto E, Nogues C, Briffod M, Bieche I, Cherel P, Garcia T, Castronovo V, Teti A, Lidereau R, & Driouch K (2008) A six-gene signature predicting breast cancer lung metastasis. Cancer Res 68(15):6092-6099.

Mimi AJ, Kang Y, Serganova I, Gupta GP, Giri DD, Doubrovin M, Ponomarev V, Gerald WI., Blasberg R, & Massague J (2005) Distinct organ-specific metastatic potential of individual breast cancer cells and primary tumors. J Clin Invest 115(1):44-55.

Zhang XH, Wang Q, Gerald W, Hudis CA, Norton I., Smid M, Foekens JA, & Massague J (2009) Latent bone metastasis in breast cancer tied to Src-dependent survival signals. Cancer Ce// 16(1):67-78.

Massague J (2007) Sorting out breast-cancer gene signatures. N Engl J Med 356(3):294-297.

Ruoslahti E (2004) Vascular zip codes in angiogenesis and metastasis. Biochem Soc Trans 32(Pt3):397-402.

Teesalu T, Sugahara KN, & Ruoslahti E (2012) Mapping of Vascular ZIP Codes by Phage Display. Methods Enzymol 503:35-56.

Powell et al., Peptide stability in drug development. II. Effect of single amino acid substitution and glycosylation on peptide reactivity in human serum. Pharm. Res. 10:1268-1273 (1993).

Brady and Dodson, Drug design. Reflections on a peptide. Nature 368:692-693 (1994).

Jameson et al., A rationally designed CD4 analogue inhibits experimental allergic encephalomyelitis. Nature 368:744-746 (1994)).

Andonegui G, et al., Mice that exclusively express TLR4 on endothelial cells can efficiently clear a lethal systemic Gram-negative bacterial infection., J Clin Invest. Jul. 2009;119(7):1921-30.

Yipp BG, et al,. Profound differences in leukocyte-endothelial cell responses to lipopolysaccharide versus lipoteichoic acid., J Immunol. May 1, 2002;168(9):4650-8.

International Search Report for PCT/CA2015/000078, dated May 14, 2015.

* cited by examiner

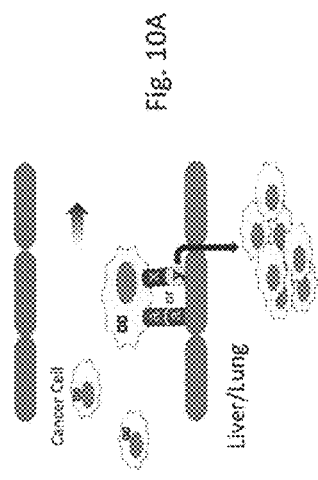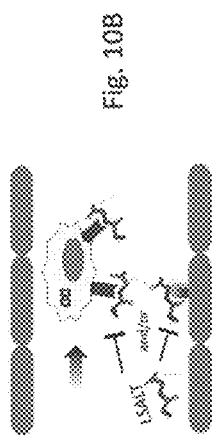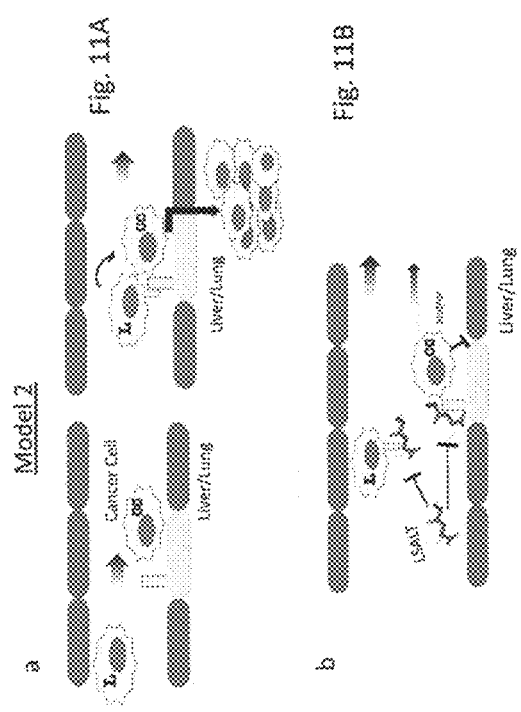

Fig. 13A        Fig. 13B        Fig. 13C
                + LSALT Peptide
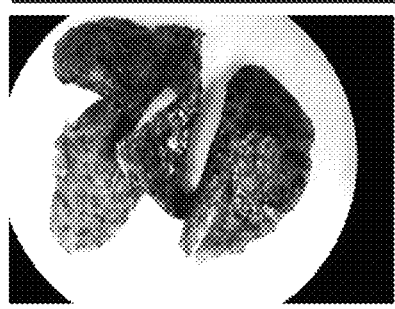 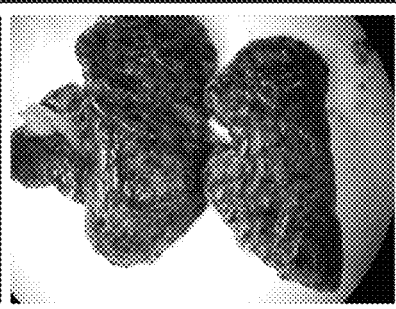 
0 μM            50 μM           500 μM
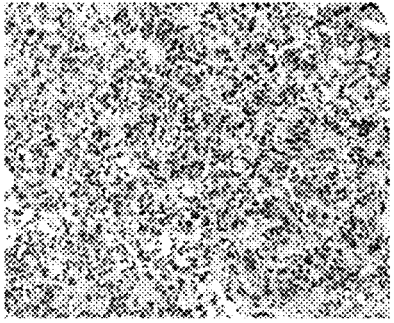 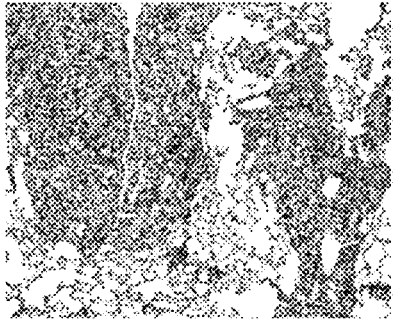 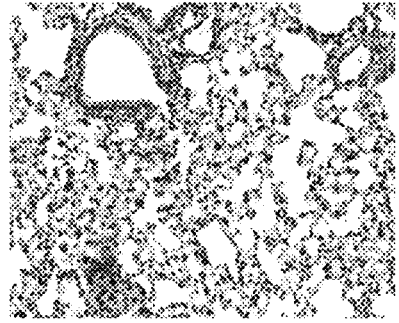
Fig. 13D        Fig. 13E        Fig. 13F Neutrophil Depletion (Anti-Ly6/GR1)

PEPTIDES THAT BLOCK LEUKOCYTE RECRUITMENT AND METHODS OF USE

CROSS REFERENCE TO RELATED APPLICATIONS

This application is a continuation of U.S. patent application Ser. No. 15/893,252 filed Feb. 9, 2018 which itself is a continuation of U.S. patent application Ser. No. 15/632,763 filed Jul. 26, 2017 which itself is a continuation of U.S. patent application Ser. No. 15/253,048 filed Aug. 31, 2016, which itself is a continuation of U.S. patent application Ser. No. 14/622,177 filed Feb. 13, 2015, now U.S. Pat. No. 9,464,114, which claims the benefit of U.S. 61/939,561 filed Feb. 13, 2014, the contents of which are incorporated by reference herein in their entirety.

FIELD OF THE INVENTION

The present invention relates to peptides capable of blocking leukocyte recruitment, and uses thereof for inhibiting tumor metastasis and for treating sepsis in a patient. More specifically, the invention relates to uses of such peptides for inhibiting tumor metastasis in the liver and lung.

BACKGROUND OF THE INVENTION

Tumors have the ability to spread to many different parts of the body but will preferentially colonize a specific set of organs and tissues (Paget S (1989) Cancer Metastasis Rev 8(2):98-101), an observation that has many clinical examples (Chiang A C & Massague J (2008) N Engl J Med 359(26):2814-2823; Nguyen D X, et al. (2009) Nat Rev Cancer 9(4):274-284). For instance, 50% of patients with uveal melanoma develop liver metastases 10-15 years after initial diagnosis (Bakalian S, et al. (2008) Clin Cancer Res 14(4):951-956; Sato T (2010) Semin Oncol 37(2):127-138). Breast cancer has the propensity to metastasize to the bone, lungs, liver and brain (Chiang A C & Massague J (2008) N Engl J Med 359(26):2814-2823; Nguyen D X, et al. (2009) Nat Rev Cancer 9(4):274-284), prostate cancer metastases almost exclusively to the bone (Scharffetter-Kochanek K, et al. (1998) J Exp Med 188(1):119-131), colorectal and pancreatic cancer tend to metastasize to the liver (Hess K R, et al. (2006) Cancer 106(7):1624-1633; Jones S, et al. (2008) Proc Nall Acad Sci USA 105(11):4283-4288) while soft tissue sarcoma spreads predominantly to the lung (Roberge D et al. (2010) Curr Oncol 17(6):18-22). Taken together, these studies highlight a real need for loco-regional management of specific cancers, a need that requires consideration of the tumor cells and the host microenvironment within a specific organ. These observations reinforce the original hypothesis from Dr. Paget that certain tumors (the "seeds") have specific affinity for particular organs ("soil") and the compatibility between the "seed" and "soil" determines the final fate of the tumor cells at that site. This premise can be expanded to incorporate the idea that the final destination of the "seed" requires the infiltrating cells of the adaptive and innate immune system to determine whether tumor cell colonization of specific organ sites will succeed or fail.

There are distinct sequential stages of the metastatic process: 1) tumor cells escape the primary tumor mass and enter the circulation either by the lymphatic system or the blood vasculature, 2) survival of the cancer cell within the circulation, 3) initial arrest within the vasculature, 4) extravasation, 5) establishment of a micrometastasis that involves the contribution of host cells within the microenvironment and 6) further growth into macrometastases, which requires adaptation of the foreign tissue microenvironment.

Using a combination of in vivo selection, genetic and pharmacological approaches, variants of breast, pancreatic and colorectal cancer have been identified that have a high propensity to metastasize to the liver ((Du Y C, et al. (2011) Proc Natl Acad Sci USA 108(40):16753-16758; Bemmo A, et al. (2010) PLoS One 5(8):e11981; Tabaries S, et al. (2011) Oncogene 30(11):1318-1328; Tabaries S, et al. (2012) Mol Cell Biol; Kang Y, et al. (2003) Cancer Cell 3(6):537-549). These variants demonstrate unique gene expression signatures and more specific target organ selectivity than the parental tumor cells (Minn A J, et al. (2005) Nature 436 (7050):518-524; Bos P D, et al. (2009) Nature 459(7249): 1005-1009; Landemaine T, et al. (2008) Cancer Res 68(15): 6092-6099; Minn A J, et al. (2005) J Clin Invest 115(1):44-55; Zhang X H, et al. (2009) Cancer Cell 16(1):67-78; Massague J (2007) N Engl J Med 356(3):294-297). These organ specific features coupled with the observation that each organ's vasculature has unique cell surface addresses or 'zip codes' (Ruoslahti E (2004) Biochem Soc Trans 32(Pt3):397-402; Teesalu T, et al. (2012) Methods Enzymol 503:35-56) raise the intriguing possibility that cancer cells can 'match' to their metastatic environment based on specific recruitment mechanisms.

What is therefore needed are compositions capable of blocking the attachment of tumor cells in the blood to the vascular supplying metastatic target organs, such as liver and lungs, to prevent or inhibit tumor metastasis to these organs. What is also needed are compositions effective to treat other diseases associated with leukocyte recruitment including sepsis such as bacterial sepsis.

SUMMARY OF THE INVENTION

Compositions comprising peptides having the ability to block leukocyte recruitment and, pharmaceutical formulations thereof are provided. Also provided are methods of reducing tumor metastasis and treating sepsis, particularly bacterial sepsis.

The invention includes, in a first aspect, an isolated peptide containing the sequence LSALTPSPSWLKYKAL, identified as SEQ ID NO: 1 (LSALT peptide).

In one embodiment, the LSALT peptide further comprises 1, 2, 3, 4, or 5 amino acid residues at the N-terminus and C-terminus of the LSALTPSPSWLKYKAL sequence.

In one embodiment, the LSALT peptide further comprises 1, 2, 3, 4, or 5 amino acid residues at the N-terminus or C-terminus of the LSALTPSPSWLKYKAL sequence.

In one embodiment, the LSALT peptide is modified by pegylation, acetylation, glycosylation, biotinylation, or substitution with one or more D-amino acid and/or un-natural amino acid.

In one embodiment, the LSALT peptide or additional residues comprise one or more modified amino acid residues or amino acid analogs.

In one embodiment, the modified amino acid residues are modified by methylation, amidation, acetylation, and/or substitution with other chemical groups.

In one embodiment, the amino acid analogs are selected from β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine.

In a second aspect, the LSALT peptide or variant thereof may be contained as an insert in a phage virus, or as a short peptide.

In a third aspect, a pharmaceutical composition is provided comprising the LSALT peptide and/or a variant thereof and pharmaceutically acceptable carrier.

In one embodiment, the carrier is selected from water, saline, phosphate buffered saline, Ringer's solution, dextrose solution, serum-containing solutions, Hank's solution, oils, esters and glycols.

In one embodiment, the pharmaceutical composition is suitable for parenteral administration. In one embodiment, the pharmaceutical composition is suitable for intravenous administration.

In a fourth aspect, the invention includes a method of inhibiting leukocyte-recruitment-mediated disease in a patient by administering to the patient a pharmaceutically effective amount of an isolated peptide containing the sequence LSALTPSPSWLKYKAL, identified as SEQ ID NO: 1.

In one embodiment, the LSALT peptide further comprises 1, 2, 3, 4, or 5 amino acid residues at the N-terminus and C-terminus of the LSALTPSPSWLKYKAL sequence.

In one embodiment, the LSALT peptide further comprises 1, 2, 3, 4, or 5 amino acid residues at the N-terminus or C-terminus of the LSALTPSPSWLKYKAL sequence.

In one embodiment, the LSALT peptide is modified by pegylation, acetylation, glycosylation, biotinylation, or substitution with one or more D-amino acid and/or un-natural amino acid.

In one embodiment, the LSALT peptide or additional residues comprise one or more modified amino acid residues or amino acid analogs.

In one embodiment, the modified amino acid residues are modified by methylation, amidation, acetylation, and/or substitution with other chemical groups.

In one embodiment, the amino acid analogs are selected from β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine.

In one embodiment, the isolated peptide or variant thereof is administered at a dosage is between about 0.01 mg/kg to 100 mg/kg.

In one embodiment, the leukocyte-recruitment-mediated disease is tumor metastasis.

In one embodiment, the isolated peptide reduces tumor metastasis compared to tumor metastasis in the absence of treatment.

In one embodiment, the invention includes a method of inhibiting tumor metastasis to the liver or lungs in a patient by administering to the patient a pharmaceutically effective amount of an isolated peptide containing the sequence LSALTPSPSWLKYKAL, identified as SEQ ID NO: 1.

In one embodiment, the isolated peptide or variant thereof is administered at a dosage is between about 0.01 mg/kg to 100 mg/kg.

In one embodiment, the leukocyte-recruitment-mediated disease is sepsis.

In one embodiment, the sepsis caused by bacterial, viral, fungal or parasite infection.

In one embodiment, the sepsis is bacterial sepsis.

In one embodiment, the invention includes a method of treating a symptom of bacterial sepsis in a patient comprising administering to the patient a pharmaceutically effective amount of an isolated peptide or variant thereof containing the sequence LSALTPSPSWLKYKAL, identified as SEQ ID NO: 1.

In one embodiment, the isolated peptide or variant thereof is administered at a dosage is between about 0.01 mg/kg to 100 mg/kg.

In one embodiment, the isolated peptide or variant thereof is administered until symptoms of bacterial sepsis are reduced or ameliorated.

In a fifth aspect, the invention includes a method of identifying a compound effective to block leukocyte recruitment in the vasculature of a patient comprising: (a) screening a library of test compounds for their ability to bind to a target peptide having a sequence selected from the group consisting of SEQ ID NOS: 2-16; (b) selecting compounds that show selective binding affinity; (c) testing the compounds for leukocyte recruitment inhibiting activity, and (d) selecting a compound if it inhibits leukocyte recruitment.

In one embodiment, the vasculature is lung vasculature or liver vasculature.

In one embodiment, the method further comprises the steps of (e) further testing the compound for its ability to inhibit tumor metastasis in an animal bearing a solid tumor; and (f) selecting the compound if it inhibits tumor metastasis in step (e).

In one embodiment, the method further comprises the steps of (e) further testing the compound for its ability to inhibit tumor metastasis to the lungs and liver in an animal bearing a solid tumor known to metastasize the lungs or liver; and (f) selecting the compound if it inhibits tumor metastasis in step (e).

In one embodiment, the method further comprises the steps of (e) further testing the compound for its ability to treat bacterial sepsis in a patient; and (f) selecting the compound if it treats sepsis in step (e).

These and other objects and features of the invention will become more fully apparent when the following detailed description of the invention is read in conjunction with the accompanying drawings.

BRIEF DESCRIPTION OF THE DRAWINGS

FIGS. 10*a* and 10*b* depict how LSALT inhibits tumor metastasis, according to a first model;

FIGS. 11*a* and 11*b* depict how LSALT inhibits tumor metastasis, according to a second model;

FIG. 13A-13F show the tumor burden in lung tissue from mice injected via tail vein with $1 \times 10^6$ 70 W human melanoma cells expressing luciferase, with or without prior injection of 50 μM or 500 μM LSALT peptide (13A-13C) and representative images of lungs with visible melanotic lung modules in mice injected via tail vein with $1 \times 10^6$ 70 W human melanoma cells expressing luciferase, with or without prior injection of 50 μM or 500 μM LSALT peptide mice (13D-13F).

DETAILED DESCRIPTION OF THE INVENTION

Definitions

Figure 1:
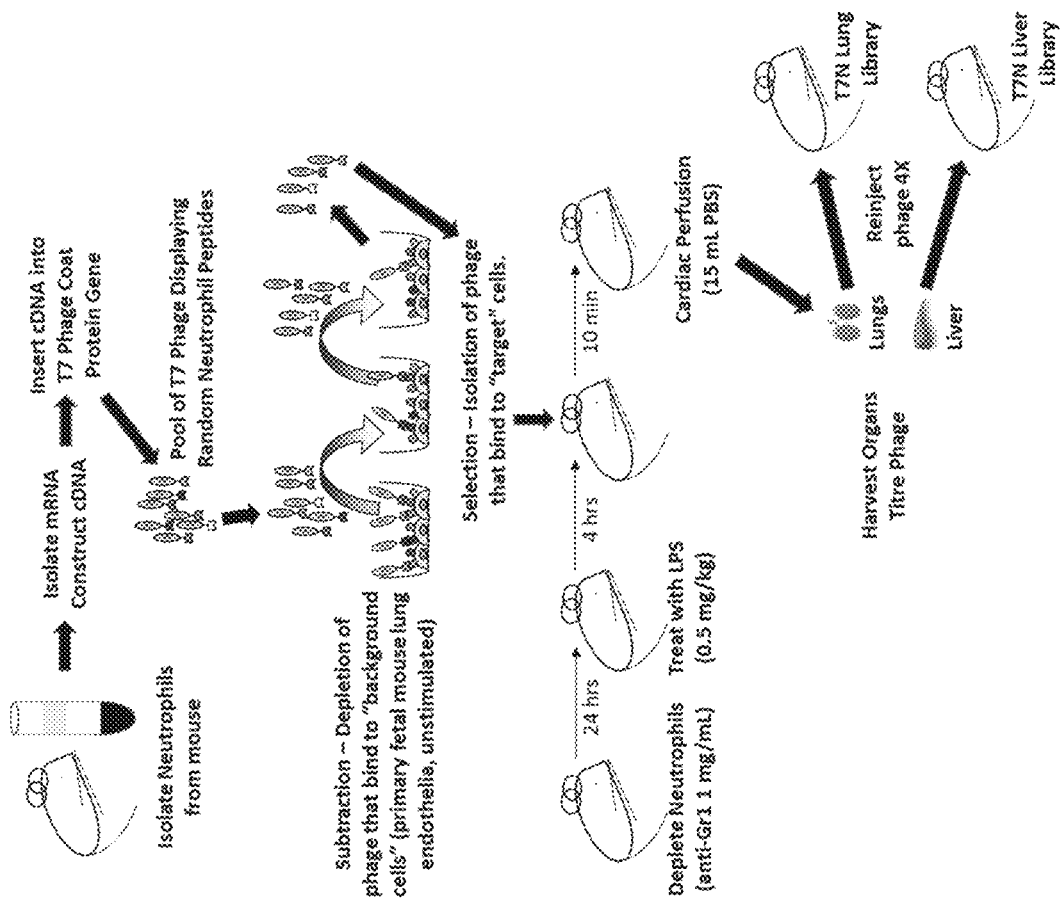
FIG. 1 is a schematic drawing that illustrates the generation of a neutrophil specific T7 phage display library, and in vivo selection and isolation of peptides that home to the liver and lung.

As used herein, the term "amino acid," in its broadest sense, refers to any compound and/or substance that can be incorporated into a polypeptide chain. The term "amino acid" is also used interchangeably with "amino acid residue," and may refer to a free amino acid and/or to an amino acid residue of a peptide. It will be apparent from the context in which the term is used whether it refers to a free amino acid or a residue of a peptide.

As used herein, "standard amino acid" refers to any of the twenty standard amino acids commonly found in naturally occurring peptides including both L- and D-amino acids which are both incorporated in peptides in nature selected from alanine, aspartate, asparagine, arginine, cysteine, glycine, glutamine, glutamate, histidine, isoleucine, leucine, lysine, methionine, proline, phenylalanine, serine, tyrosine, threonine, tryptophan and valine. "Nonstandard" or "unconventional amino acid" refers to any amino acid, other than the standard amino acids, regardless of whether it is prepared synthetically or obtained from a natural source. As used herein, "synthetic or un-natural amino acid" encompasses chemically modified amino acids, including but not limited to salts, amino acid derivatives (such as amides), and/or substitutions.

I. Peptides

The present invention is based on the discovery of non-naturally-occurring peptides that reduces leukocyte recruitment and therefore has utility for treating leukocyte-recruitment-mediated diseases, for example, tumor metastasis and sepsis. Variants and modified embodiments of this peptide that are capable of reducing leukocyte recruitment are also provided.

Using an unbiased combinatorial phage in vivo biopanning approach, a specific peptide-displaying-phage was isolated that localized to the liver and lungs of animals treated with a pro-inflammatory stimulus and blocks leukocyte recruitment. This phage and its corresponding displayed peptide (N-LSALTPSPSWLKYKAL called LSALT, identified herein as SEQ ID NO:1) were also found to dramatically reduce tumor burden in the livers or lungs of animals injected with a tumor cell line. The peptide also reduced neutrophil recruitment to the liver in a mouse model of sepsis.

The LSALT peptide, as well as variants and modified versions thereof are described herein. Also described are pharmaceutical compositions comprising these peptides.

In some embodiments, the LSALT peptide contains one or more modifications to increase protease resistance, serum stability and/or bioavailability. In some embodiments, the modification is selected from pegylation, acetylation, glycosylation, biotinylation, substitution with D-amino acid and/or un-natural amino acid, and/or cyclization of the peptide.

In certain embodiments, the LSALT peptide contains one or more L-amino acids, D-amino acids, and/or non-standard amino acids.

In certain embodiments, the amino acid has the general structure $H_2N-C(H)(R)-COOH$. In certain embodiments, the amino acid is a naturally-occurring amino acid. In certain embodiments, the amino acid is a synthetic or un-natural amino acid (e.g., α,α-disubstituted amino acids, N-alkyl amino acids); in some embodiments, the amino acid is a d-amino acid; in certain embodiments, the amino acid is an l-amino acid.

In one embodiment, the peptide comprises amino acids, including carboxy- and/or amino-terminal amino acids in peptides, or can be modified by methylation, amidation, acetylation, and/or substitution with other chemical groups that can change the peptide's circulating half-life without adversely affecting its activity. Examples of unconventional or un-natural amino acids include, but are not limited to, citrulline, ornithine, norleucine, norvaline, 4-(E)-butenyl-4 (R)-methyl-N-methylthreonine (MeBmt), N-methyl-leucine (MeLeu), aminoisobutyric acid, statine, and N-methyl-alanine (MeAla). Amino acids may participate in a disulfide bond.

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., Current Protocols in Molecular Biology, Wiley Interscience, New York, 2001; and Sambrook et al., Molecular Cloning: A Laboratory Manual, 3rd edition, Cold Spring Harbor Laboratory Press, N.Y., 2001.

While peptides may be effective in eliciting a biological activity in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., Pharm. Res. 10:1268-1273 (1993)). In light of this, it is often advantageous to use modified versions of peptides. The modified peptides retain the structural characteristics of the original L-amino acid peptides that confer the desired biological activity of LSALT but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides. Thus, a peptide derivative or peptidomimetic of the present invention may be all L, all D or mixed D, L peptide, in either forward or reverse order. The presence of an N-terminal or C-terminal D-amino acid increases the in vivo stability of a peptide since peptidases cannot utilize a D-amino acid as a substrate (Powell et al., Pharm. Res. 10:1268-1273 (1993)). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides retain the same secondary conformation and therefore similar activity, as the L-amino acid peptides, but are more resistant to enzymatic degradation in vitro and in vivo, and thus can have greater therapeutic efficacy than the original peptide (Brady and Dodson, Nature 368:692-693 (1994); Jameson et al., Nature 368:744-746 (1994)). Similarly, a reverse-L peptide may be generated using standard methods where the C-terminus of the parent peptide becomes takes the place of the N-terminus of the reverse-L peptide. It is contemplated that reverse L-peptides of L-amino acid peptides that do not have significant secondary structure (e.g., short peptides) retain the same spacing and conformation of the side chains of the L-amino acid peptide and therefore often have the similar activity as the original L-amino acid peptide. Moreover, a reverse peptide may contain a combination of L- and D-amino acids. The spacing between amino acids and the conformation of the side chains may be retained resulting in similar activity as the original L-amino acid peptide.

In one embodiment, the peptide is chemically modified to confer resistance to peptidases acting on the N-terminal or C-terminal residues of a peptide by adding chemical groups at the peptide termini, such that the modified peptide is no longer a substrate for the peptidase. In one embodiment, one such chemical modification is glycosylation of the peptides at either or both termini. In other embodiments, chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified peptides consisting of peptides bearing an N-terminal acetyl group and/or a C-terminal amide group.

In one embodiment, substitution of certain naturally-occurring amino acids for non-naturally amino acids in the peptides confers resistance to proteolysis. Such a substitution can, for instance, confer resistance to proteolysis by exopeptidases acting on the N-terminus without affecting biological activity. Examples of non-naturally-occurring amino acids include α,α-disubstituted amino acids, N-alkyl amino acids, C-α-methyl amino acids, β-amino acids, and β-methyl amino acids. Amino acids analogs useful in the present invention may include, but are not limited to, β-alanine, norvaline, norleucine, 4-aminobutyric acid, orithine, hydroxyproline, sarcosine, citrulline, cysteic acid, cyclohexylalanine, 2-aminoisobutyric acid, 6-amino-hexanoic acid, t-butylglycine, phenylglycine, o-phosphoserine, N-acetyl serine, N-formylmethionine, 3-methylhistidine and other unconventional amino acids. Furthermore, the synthesis of peptides with non-naturally-occurring amino acids is known in the art.

In various embodiments, the LSALT peptide further comprises amino acid residues or analogues at the C-terminus, the N-terminus or both the C-terminus and the N-terminus. Preferably the activity bearing sequence of the LSALT peptide is not appreciably impacted by the addition of these additional amino acid.

In one embodiment, the LSALT peptide, further comprises 1, 2, 3, 4, or 5 amino acid residues at the N-terminus and C-terminus of the LSALT peptide.

In another embodiment, the LSALT peptide, further comprises 1, 2, 3, 4, or 5 amino acid residues at the N-terminus of the LSALTPSPSWLKYKAL sequence.

In another embodiment, the LSALT peptide, further comprises 1, 2, 3, 4, or 5 amino acid residues at the C-terminus of the LSALTPSPSWLKYKAL sequence.

In various embodiments, the peptide is selected from XLSALTPSPSWLKYKAL, XXLSALTPSPSWLKYKAL, XXXLSALTPSPSWLKYKAL, XXXXLSALTPSPSWLKYKAL, or XXXXXLSALTPSPSWLKYKAL, where X is any naturally-occurring amino acid or where X is an unconventional amino acid or amino acid analog as described herein and known to those of skill in the art.

In various embodiments, the peptide is selected from LSALTPSPSWLKYKALX, LSALTPSPSWLKYKALXX, LSALTPSPSWLKYKALXXX, LSALTPSPSWLKYKALXXXX, or LSALTPSPSWLKYKALXXXXX, where X is any naturally-occurring amino acid or where X is an unconventional amino acid or amino acid analog as described herein and known to those of skill in the art.

In various embodiments, the peptide is selected from XLSALTPSPSWLKYKALX, XLSALTPSPSWLKYKALXX, XLSALTPSPSWLKYKALXXX, XLSALTPSPSWLKYKALXXXX, XLSALTPSPSWLKYKALXXXXX, XXLSALTPSPSWLKYKALX, XXLSALTPSPSWLKYKAXX, XXLSALTPSPSWLKYKALXXX, XXLSALTPSPSWLKYKA- LXXXX, XXLSALTPSPSWLKYKALXXXXX, XXXL-SALTPSPSWLKYKALX, XXXLSALTPSPSWLKYKALXX, XXXLSAL-TPSPSWLKYKALXXX, XXXLSALTPSPSWLKYKA-LXXXX, XXXLSALTPSPSWLKYKALXXXXX, XXXXLSALTPSPSWLKYKALX, XXXXLSAL-TPSPSWLKYKALXX, XXXXLSALTPSPSWLKYKA-LXXX XXXXLSALTPSPSWLKYKALXXXX, XXXXL-SALTPSPSWLKYKALXXXXX, XXXXXLSALTPSPSW emulsifiers, salts for influencing osmotic pressure, buffers, coloring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, sustained release formulation, or powder. The composition can also be formulated as a suppository, with traditional binders and carriers such as triglycerides.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, the pharmaceutical composition comprise a liquid carrier such as, but not limited to, water, saline, phosphate buffered saline, Ringer's solution, dextrose solution, serum-containing solutions, Hank's solution, other aqueous physiologically balanced solutions, oils, esters and glycols.

The LSALT peptide as described herein can be formulated as neutral or salt forms. As stated above, pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The pharmaceutical formulations of the present invention contain, as the active ingredient, an LSALT peptide, which may be mixed with an excipient, diluted by an excipient or enclosed within a carrier, which can be in the form of a capsule, sachet, paper or other container, according to well-known methods and pharmaceutical compositions. The composition may be administered by any route suitable for peptide administration, including parenteral, intravenous, subcutaneous, or intramuscular administration. Typically, the peptide is dissolved or suspended in a sterile injectable solution, at a concentration sufficient to provide the required dose in 0.5 to 2 ml or less. Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable materials can be sterilized for example, by filtration through a bacterial-retaining filter.

The pharmaceutical compositions may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

III. Kits

In some embodiments, the present invention further provides kits or other articles of manufacture which contain the LSALT peptide or pharmaceutical compositions described herein, as well as instructions for its reconstitution (if lyophilized) and/or use. Kits or other articles of manufacture may include a container, a syringe, vial and any other articles, devices or equipment useful in administration (e.g., subcutaneous, by inhalation). Suitable containers include, for example, bottles, vials, syringes (e.g., pre-filled syringes), ampules, cartridges, reservoirs, or lyo-jects. The container may be formed from a variety of materials such as glass or plastic. In some embodiments, the container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, the container may contain a single dose of a stable formulation containing an LSALT peptide. In various embodiments, a single dose of the stable formulation is present in a volume of less than about 15 ml, about 10 ml, about 5.0 ml, about 4.0 ml, about 3.5 ml, about 3.0 ml, about 2.5 ml, about 2.0 ml, about 1.5 ml, about 1.0 ml, or about 0.5 ml. Alternatively, the container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least about 1 mg/ml (e.g., at least about 5 mg/ml, at least about 10 mg/ml, at least about 20 mg/ml, at least about 30 mg/ml, at least about 40 mg/ml, at least about 50 mg/ml, at least about 75 mg/ml, at least about 100 mg/ml). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

IV. Dosage

When employed as pharmaceuticals, the peptides of the present invention are administered in the form of pharmaceutical compositions and these pharmaceutical compositions represent further embodiments of the present invention. These compounds can be administered by a variety of routes including oral, rectal, transdermal, subcutaneous, intravenous, intramuscular, and intranasal, or via intratracheal instillation or aerosol inhalation.

The peptides of the invention are useful in blocking or inhibiting tumor metastasis, e.g., into the liver manner of administration will be defined by the application of the compound and can be determined by routine methods of clinical testing to find the optimum dose.

In one embodiment, the dosage is between about 0.01 mg/kg to about 100 mg/kg of active peptide, between about 0.01 mg/kg to about 50 mg/kg, or between about 0.01 mg/kg to about 25 mg/kg.

In other embodiments, the dosage is between about 0.1 mg/kg to about 100 mg/kg, between about 0.1 mg/kg to about 50 mg/kg, between about 0.1 mg/kg to about 25 mg/kg, or between about 0.1 mg/kg to about 10 mg/kg.

In other embodiments, the dosage is between about 0.5 mg/kg to about 100 mg/kg, about 0.5 mg/kg to about 50 mg/kg, about 0.5 mg/kg to about 25 mg/kg, or about 0.5 mg/kg to about 10.0 mg/kg.

In other embodiments, the dosage is between about 1.0 mg/kg to about 25 mg/kg, between about 1.0 mg/kg to about 50 mg/kg, between about 1.0 mg/kg to about 70 mg/kg, between about 1.0 mg/kg to about 100 mg/kg, between about 5.0 mg/kg to about 25 mg/kg, between about 5.0 mg/kg to about 50 mg/kg, between about 5.0 mg/kg to about 70 mg/kg, between about 5.0 mg/kg to about 100 mg/kg, between about 10.0 mg/kg to about 25 mg/kg, between about 10.0 mg/kg to about 50 mg/kg, between about 10.0 mg/kg to about 70 mg/kg, or between about 10.0 mg/kg to about 100 mg/kg.

In another embodiment, the dosage is between about 50 µM and about 500 µM.

It will be understood, however, that the amount of the peptide actually administered will be determined by a physician, in the light of the relevant circumstances, including the condition to be treated, the chosen route of administration, the actual compound administered, the age, weight, and response of the individual patient, the severity of the patient's symptoms, and the like.

In various embodiments, peptides and/or proteins described herein, or salts thereof, are administered in amounts between about 0.001 and about 20 mg/kg body weight per day, between about 0.01 and about 10 mg/kg body weight per day, between about 0.1 and about 1000 µg/kg body weight per day, or between about 0.1 to about 100 µg/kg body weight per day. Routes of administration vary. For example, peptides and/or proteins described herein, or salts thereof, are administered in amounts between about 0.1 and about 1000 µg/kg body weight per day, or between about 0.1 to about 100 µg/kg body weight per day, by subcutaneous injection. By way of example, for a 50 kg human female subject, the daily dose of active ingredient is from about 5 to about 5000 µg, or from about 5 to about 5000 µg by subcutaneous injection. Different doses will be needed, depending on the route of administration, the compound potency, the pharmacokinetic profile and the applicable bioavailability observed, and the active agent and the disease being treated. In an alternate embodiment where the administration is by inhalation, the daily dose is from 1000 to about 20,000 µg, twice daily. In other mammals, such as horses, dogs, and cattle, higher doses may be required. This dosage may be delivered in a conventional pharmaceutical composition by a single administration, by multiple applications, or via controlled release, as needed to achieve the most effective results.

V. Methods of Manufacture

The LSALT peptides or derivatives described herein may be obtained by any method of peptide synthesis known to those skilled in the art, including synthetic (e.g., exclusive solid phase synthesis, partial solid phase synthesis, fragment condensation, classical solution synthesis, native-chemical ligation) and recombinant techniques. For example, the peptides or peptides derivatives can be obtained by solid phase peptide synthesis, which in brief, consist of coupling the carboxyl group of the C-terminal amino acid to a resin (e.g., benzhydrylamine resin, chloromethylated resin, hydroxymethyl resin) and successively adding N-alpha protected amino acids. The protecting groups may be any such groups known in the art. Before each new amino acid is added to the growing chain, the protecting group of the previous amino acid added to the chain is removed. Such solid phase synthesis has been disclosed, for example, by Merrifield, J. Am. Chem. Soc. 85: 2149 (1964); Vale et al., Science 213:1394-1397 (1981), in U.S. Pat. Nos. 4,305,872 and 4,316,891, Bodonsky et al. Chem. Ind. (London), 38:1597 (1966); and Pietta and Marshall, Chem. Comm. 650 (1970) by techniques reviewed in Lubell et al. "Peptides" Science of Synthesis 21.11, Chemistry of Amides. Thieme, Stuttgart, 713-809 (2005). The coupling of amino acids to appropriate resins is also well known in the art and has been disclosed in U.S. Pat. No. 4,244,946. (Reviewed in Houver-Weyl, Methods of Organic Chemistry. Vol E22a. Synthesis of Peptides and Peptidomimetics, Murray Goodman, Editor-in-Chief, Thieme. Stuttgart. N.Y. 2002).

During any process of the preparation of the LSALT peptide, it may be desirable to protect sensitive reactive groups on any of the molecule concerned. This may be achieved by means of conventional protecting groups such as those described in Protective Groups In Organic Synthesis by T. W. Greene & P. G. M. Wuts, 1991, John Wiley and Sons, New-York; and Peptides: chemistry and Biology by Sewald and Jakubke, 2002, Wiley-VCH, Wheinheim p. 142. For example, alpha amino protecting groups include acyl type protecting groups (e.g., trifluoroacetyl, formyl, acetyl), aliphatic urethane protecting groups (e.g., t-butyloxycarbonyl (BOC), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl). The amino acids side chain protecting groups include benzyl (for Thr and Ser), Cbz (Tyr, Thr, Ser, Arg, Lys), methyl ethyl, cyclohexyl (Asp, His), Boc (Arg, His, Cys) etc. The protecting groups may be removed at a convenient subsequent stage using methods known in the art.

Further, the LSALT peptide may be synthesized according to the FMOC protocol in an organic phase with protective groups. Desirably, the peptides are purified with a yield of 70% with high-pressure liquid chromatography (HPLC) on a C18 chromatography column and eluted with an acetonitrile gradient of 10-60%. The molecular weight of a peptide can be verified by mass spectrometry (reviewed in Fields, G. B. "Solid-Phase Peptide Synthesis" Methods in Enzymology. Vol. 289, Academic Press, 1997).

Alternatively, the LSALT peptide may be prepared in recombinant systems using, for example, polynucleotide sequences encoding the polypeptides. It is understood that a polypeptide may contain more than one of the above-described modifications within the same polypeptide.

VI. Characterization of the LSALT Peptide

Although the LSALT peptide is not naturally-occurring, BLAST analysis of the LSALT peptide found it had similarities to: double cortin; fibulin-2; -Fermt3; -tetraspannin 18; -shroom3; -sorting nexin 8; -FGFR-3; -Protogenin homologue; -myomesin 3; and -prdml6.

When the LSALT phage was immobilized on nitrocellulose and biopanned against with a combinatorial M13 phage library, the following peptides were isolated as peptides that bind specifically with the LSALT. These peptides provide potential targets for action of LSALT peptides, variants and modifications thereof.

TABLE 1

Putative targets of LSALT

| Target Sequence | SEQ ID NO: |
|---|---|
| HLPSIIPTMPYR | (SEQ ID NO: 2) |
| EQFTNLLDMYTA | (SEQ ID NO: 3) |
| IPPSYSATLPALR | (SEQ ID NO: 4) |
| EQFTNLLDMTYA | (SEQ ID NO: 5) |
| HATGTHGLSLSH | (SEQ ID NO: 6) |
| TNITESQQLNWR | (SEQ ID NO: 7) |
| FEQKKGT | (SEQ ID NO: 8) |
| DNTRVDT | (SEQ ID NO: 9) |
| PTLPWKK | (SEQ ID NO: 10) |
| MNVTPRQ | (SEQ ID NO: 11) |
| TTEHPRK | (SEQ ID NO: 12) |
| LGPAHLY | (SEQ ID NO: 13) |
| GLHNKTH | (SEQ ID NO: 14) |
| LNTQTGK | (SEQ ID NO: 15); |
| NERNSWH | (SEQ ID NO: 16) |

As considered below, all of these peptides are potential targets for compounds, e.g., peptide compounds that will be therapeutically effective in blocking neutrophil recruitment in the liver or lungs, for purposes of inhibiting tumor metastasis to the liver or lungs, and for the treatment of sepsis.

VII. Screening Methods

Thus, in accordance with one aspect of the invention, there is provided a method for identifying a compound effective to block leukocyte recruitment in the vasculature of a patient. The method includes screening a library of test compounds for their ability to bind to a target peptide having a sequence selected from the group consisting of SEQ ID NOS: 2-16. For those library compounds that show a selective binding affinity to one of the target peptides in the library, e.g., at least a 10-100 fold increase in binding affinity over a random-sequence peptide, the compound is further testing for its ability to inhibit leukocyte recruitment, according to methods detailed below. Test compounds that are shown to block leukocyte recruitment are then identified as lead compounds for further compound testing and development.

In one embodiment, the invention provides a method of identifying a compound effective to block leukocyte recruitment in the vasculature of a patient comprising: (a) screening a library of test compounds for their ability to bind to a target peptide having a sequence selected from the group consisting of SEQ ID NOS: 2-16; (b) selecting compounds that show selective binding affinity; (c) testing the compounds for leukocyte recruitment inhibiting activity, and (d) selecting a compound if it inhibits leukocyte recruitment.

In one embodiment, the vasculature is lung vasculature or liver vasculature.

In one embodiment, the method further comprises the steps of (e) further testing the compound for its ability to inhibit tumor metastasis in an animal bearing a solid tumor; and (f) selecting the compound if it inhibits tumor metastasis in step (e).

In one embodiment, the method further comprises the steps of (e) further testing the compound for its ability to inhibit tumor metastasis to the lungs and liver in an animal bearing a solid tumor known to metastasize the lungs or liver; and (f) selecting the compound if it inhibits tumor metastasis in step (e).

In one embodiment, the method further comprises the steps of (e) further testing the compound for its ability to treat bacterial sepsis in a patient; and (f) selecting the compound if it treats sepsis in step (e).

In one embodiment, step (a) in the method includes screening a library of test compounds for their ability to bind to a target peptide having a sequence selected from the group consisting of SEQ ID NOS: 2-7.

In another embodiment step (a) includes screening a library of test compounds for their ability to bind to a target peptide having a sequence selected from the group consisting of SEQ ID NOS: 8-16.

VIII. LSALT Mechanism of Action

Without intending to be bound by any particular mechanism, it is believed that the ability of LSALT to block neutrophil recruitment to liver and lung sinusoids could occur by one of two mechanisms of action, which are illustrated in FIGS. 10 and 11. Model 1 (FIG. 10) depicts cancer cells (cc in the figure) having a specific adhesion molecule that is shared by neutrophils, e.g., leukocytes, which mediates the binding of the cancer cells to the endothelium in the target vasculature, and the extravasation of the cancer cells through the endothelium layer. Binding of LSALT to this factor abrogates binding of the cancer cells to the endothelium and/or extravasation into the target-tissue, e.g., liver.

A second model, as shown in FIG. 11, proposes that the cancer cells bind to the endothelium but require leukocytes to provide the ability to extravasate into the target organ. The LSALT peptide in this model works by blocking recruitment of the leukocytes to the proximity of the cancer cells, or blocking the interaction of the leukocytes with the cancer cells.

These two models are not mutually exclusive and more complex models could be invoked that require the integration of both. While not to be bound by any specific mechanism and based on the observation that the isolated phage and its corresponding displayed peptide are able to inhibit the recruitment of endogenous leukocytes and two different models of tumor cell metastasis (both mouse and human), it appears likely that the LSALT peptide interferes with the earlier stages of metastasis, specifically the initial arrest/recruitment of the cancer cell within the vasculature and/or their extravasation into the surrounding tissue.

IX. Methods of Treatment

As used herein, "Treating" or "treatment" refers to inhibiting the disease or condition, i.e., arresting or reducing its development or at least one clinical or subclinical symptom thereof. "Treating" or "treatment" further refers to relieving the disease or condition, i.e., causing regression of the disease or condition or at least one of its clinical or subclinical symptoms. The benefit to a patient to be treated is either statistically significant or at least perceptible to the patient and/or the physician.

In one aspect, the invention includes a method of inhibiting leukocyte-recruitment-mediated disease in a patient by administering to the patient a pharmaceutically effective amount of an isolated peptide containing the sequence LSALTPSPSWLKYKAL, identified as SEQ ID NO: 1.

In one embodiment, the LSALT peptide further comprises 1, 2, 3, 4, or 5 amino acid residues at the N-terminus and C-terminus of the LSALTPSPSWLKYKAL sequence.

In one embodiment, the LSALT peptide further comprises 1, 2, 3, 4, or 5 amino acid residues at the N-terminus or C-terminus of the LSALTPSPSWLKYKAL sequence.

In various embodiments, the peptide is selected from XLSALTPSPSWLKYKAL, XXLSALTPSPSWLKYKAL, XXXLSALTPSPSWLKYKAL, XXXXLSALTPSPSWLKYKAL, or XXXXXLSALTPSPSWLKYKAL, where X is any naturally-occurring amino acid or where X is an unconventional amino acid or amino acid analog as described herein and known to those of skill in the art.

In various embodiments, the peptide is selected from LSALTPSPSWLKYKALX, LSALTPSPSWLKYKALXX, LSALTPSPSWLKYKALXXX, LSALTPSPSWLKYKALXXXX, or LSALTPSPSWLKYKALXXXXX, where X is any naturally-occurring amino acid or where X is an unconventional amino acid or amino acid analog as described herein and known to those of skill in the art.

In various embodiments, the peptide is selected from XLSALTPSPSWLKYKALX, XLSALTPSPSWLKYKALXX, XLSALTPSPSWLKYKALXXX, XLSALTPSPSWLKYKALXXXX, XLSALTPSPSWLKYKALXXXXX, XXLSALTPSPSWLKYKALX, XXLSALTPSPSWLKYKAXX, XXLSALTPSPSWLKYKALXXX, XXLSALTPSPSWLKYKALXXXX, XXLSALTPSPSWLKYKALXXXXX, XXXLSALTPSPSWLKYKALX, XXXLSALTPSPSWLKYKALXX, XXXLSALTPSPSWLKYKALXXX, XXXLSALTPSPSWLKYKALXXXX, XXXLSALTPSPSWLKYKALXXXXX, XXXXLSALTPSPSWLKYKALX, XXXXLSALTPSPSWLKYKALXX, XXXXLSALTPSPSWLKYKALXXX XXXXLSALTPSPSWLKYKALXXXX, XXXXLSALTPSPSWLKYKALXXXXX, XXXXXLSALTPSPSWLKYKALX, XXXXXLSALTPSPSWLKYKALXX, XXXXXLSALTPSPSWLKYKALXXX XXXXXLSALTPSPSWLKYKALXXXX, or XXXXXLSALTPSPSWLKYKALXXXXX, where X is any naturally-occurring amino acid or where X is an unconventional amino acid or amino acid analog as described herein and known to those of skill in the art.

In one embodiment, the peptide is modified by pegylation, acetylation, glycosylation, biotinylation, or substitution with one or more D-amino acid and/or un-natural amino acid.

In one embodiment, the peptide or additional residues comprise one or more modified amino acid residues or amino acid analogs.

In one embodiment, the modified amino acid residues are modified by methylation, amidation, acetylation, and/or substitution with other chemical groups.

In one embodiment, the amino acid analogs are selected from β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine.

In one embodiment, the isolated peptide or variant thereof is administered at a dosage is between about 0.01 mg/kg to 100 mg/kg.

In one aspect, the leukocyte-recruitment-mediated disease is tumor metastasis.

In one embodiment, the isolated peptide reduces tumor metastasis compared to tumor metastasis in the absence of treatment.

In one embodiment, the invention includes a method of inhibiting tumor metastasis to the liver or lungs in a patient by administering to the patient a pharmaceutically effective amount of an isolated peptide containing the sequence LSALTPSPSWLKYKAL, identified as SEQ ID NO: 1.

In one embodiment, the isolated peptide or variant thereof is administered at a dosage is between about 0.01 mg/kg to 100 mg/kg.

The peptide is administered to a subject having a solid tumor that has the potential to metastasize to the liver or lungs. The peptide is preferably administered at least once, preferably at least two times/week, at the above therapeutic dose, and the treatment may be maintained until the solid tumor itself has been effectively treated, e.g., by a combination of surgical resection and radiation.

Figure 12:
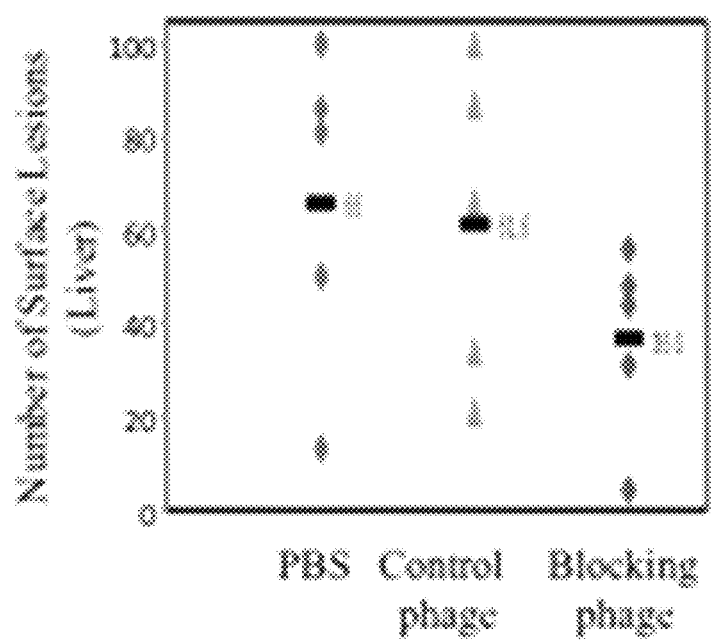
FIG. 12 shows data from a study in which intrasplenic injection of 4T1 murine breast cancer cells was performed in the presence or absence of control phage of LSALT expressing phage, and the number of surface mammary tumor metastasis were assessed in the liver 4-week post injection.

FIG. 12 shows data from a study in which intrasplenic injection of 4T1 murine breast cancer cells was performed in the presence or absence of control phage of LSALT expressing phage, and the number of surface mammary tumor metastasis were assessed in the liver 4-week post injection. As seen, the LSALT peptide significantly reduced the number of neutrophils present in liver sinusoid tissue.

In one treatment study, $1\times10^6$ 70 W $1\times10^6$ human melanoma cells expressing luciferase were injected via tail vein with or without prior injection of 50 μM or 500 μM LSALT peptide. 4 weeks post-injection, animals were sacrificed and the lungs were removed and assessed for tumor burden (FIG. 13A-13F) or imaged using the Xenogen light-emission system (FIGS. 14A-14D) FIGS. 13A-13C show representative images of lungs, with visible melanotic lung nodules occurring least frequently in the animal receiving the highest dose of LSALT. FIGS. 13A-13C show frozen lung sections stained with human nucleolin (brown) and counterstained with toludine blue (top row), and FIGS. 13D-13F show excised lungs with tumor cells expressing melanin (brown) demonstrating tumor burden in the lungs, with the tissue showing highest levels of LSALT showing the least tumor burden.

Figures 14A, 14B:
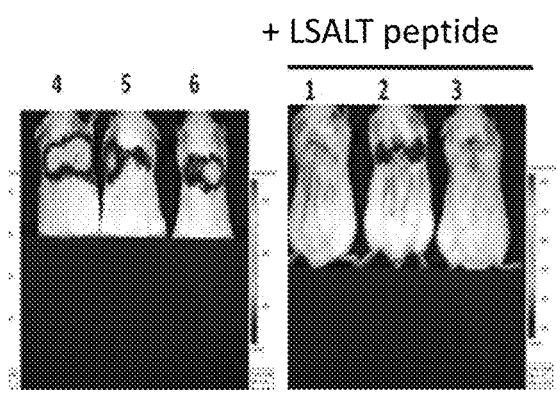
FIG. 14A-14D show Xenogen images of lungs from mice injected via tail vein with human melanoma cells expressing luciferase with (14B) and without (14A) pretreatment with LSALT; and Xenogen images of lungs from mice injected treated as described for FIGS. 13A and 13B, and in the presence (14D) and absence (14C) of neutrophil depletion using anti-Ly6G/GRI antibody.
Figures 14C, 14D:
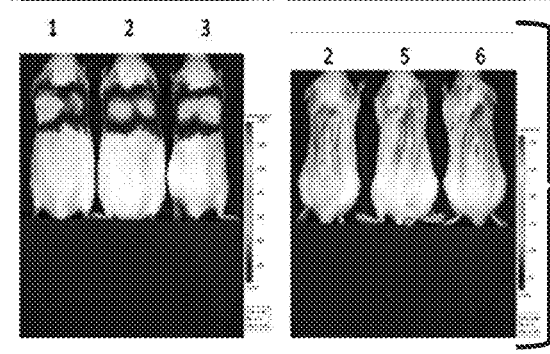

Animals were treated as above in the absence or presence of Neutrophil depletion using Anti-Ly6G/GR1, and the animals were imaged with the Xenogen light system. As can be seen in FIGS. 14A and 14B, progressively greater amounts LSALT produced progressively less tumor burden and the same result was seen when the animals were pretreated for neutrophil depletion (FIGS. 14C and 14D).

In one aspect, the leukocyte-recruitment-mediated disease is sepsis.

In one embodiment, the sepsis caused by bacterial, viral, fungal or parasite infection.

In one embodiment, the sepsis is bacterial sepsis.

In one embodiment, the invention includes a method of treating a symptom of bacterial sepsis in a patient comprising administering to the patient a pharmaceutically effective amount of an isolated peptide or variant thereof containing the sequence LSALTPSPSWLKYKAL, identified as SEQ ID NO: 1.

In one embodiment, the isolated peptide or variant thereof is administered at a dosage is between about 0.01 mg/kg to 100 mg/kg.

In one embodiment, the isolated peptide or variant thereof is administered until symptoms of bacterial sepsis are reduced or ameliorated.

In another aspect, the invention includes a includes a method of treating bacterial sepsis, by administering to the patient, a pharmaceutically effective amount of an isolated peptide containing the sequence LSALTPSPSWLKYKAL, identified as SEQ ID NO: 1. As above, the peptide may be the 16mer peptide, a 16-26mer peptide containing 0-5 additional amino acid residues at one or both termini of the peptide or a phage particle containing the LSALT peptide as an insert. The peptide is administered to a subject having bacterial sepsis. Treatment is preferably administration once a day, at the above dose, until the bacterial infection has been treated and the risk of sepsis has passed.

X. Routes of Administration

An LSALT peptide as described herein (or a composition or medicament containing LSALT peptide as described herein) may be administered by any appropriate route. In some embodiments, the LSALT peptide is administered parenterally. In some embodiments, the parenteral administration is selected from intravenous, intradermal, inhalation, transdermal (topical), intraocular, intramuscular, subcutaneous, intramuscular, and/or transmucosal administration. In some embodiments, an LSALT peptide as described herein is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an LSALT peptide as described herein is administered intravenously. In other embodiments, an LSALT peptide as described herein is administered by direct administration to a target tissue, such as heart or muscle (e.g., intramuscular), tumor (intratumorally), nervous system (e.g., direct injection into the brain; intraventricularly; intrathecally). Alternatively, an LSALT peptide as described herein (or a composition or medicament containing an LSALT peptide as described herein) can be administered by inhalation, parenterally, intradermally, transdermally, or transmucosally (e.g., orally or nasally). More than one route can be used concurrently, if desired.

In some embodiments, an LSALT peptide as described herein is administered orally. In some embodiments, the present invention provides solid dosage forms of LSALT peptide as described herein for oral administration including (a) an LSALT peptide, (b) at least one pharmaceutically acceptable pH-lowering agent, (c) at least one absorption enhancer effective to promote bioavailability of the LSALT peptide, and (d) a protective vehicle. In some embodiments, the solid dosage form is a capsule or tablet. Various methods and ingredients for making oral formulations are known in the art and it is expected that one of skill would be able to determine which of these methods and ingredients will be compatible with the invention as described in this specification and/or in U.S. Provisional Patent Application Ser. No. 61/61/939,561, filed on Feb. 13, 2014, the disclosure of which is hereby incorporated in its entirety. Such methods and ingredients are also contemplated as within the scope of the present invention.

XI. Dosing Schedules

Various embodiments may include differing dosing regimen. In some embodiments, the LSALT peptide is administered via continuous infusion. In some embodiments, the continuous infusion is intravenous. In other embodiments, the continuous infusion is subcutaneous. Alternatively or additionally, in some embodiments, the LSALT peptide is administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

XII. Methods of Screening

In a third aspect, the invention includes a method of identifying a compound effective to block leukocyte recruitment in the vasculature of a patient.

In one embodiment, the vasculature is of the lungs or liver of the patient.

In one embodiment, the method includes the steps of (a) screening a library of test compounds for their ability to bind to a target peptide having a sequence selected from the group consisting of SEQ ID NOS: 2-16; (b) for those library compounds that show a selective binding affinity to one of the target peptides in the library; further testing the compound for its ability to inhibit tumor metastasis to the lungs or liver in an animal bearing a solid tumor known to metastasize the lungs or liver; and (c) selecting the compound if it inhibits tumor metastasis in step (b).

In one embodiment, the method includes a use for identifying a compound effective to inhibit tumor metastasis to the lungs or liver in a patient, the method further includes, in step (b), testing the compound for its ability to inhibit tumor metastasis to the lungs and liver in an animal bearing a solid tumor known to metastasize the lungs and liver.

In one embodiment, the method includes a use for identifying a compound effective to treat bacterial sepsis in a patient, the method further includes in step (b) testing the compound for its ability to treat sepsis in an animal model.

All publications and patent applications mentioned in this specification are herein incorporated by reference to the same extent as if each independent publication or patent application is specifically and individually indicated to be incorporated by reference.

EXAMPLES

Example 1: Preparation of T7 Liver and Lung Phage Display Libraries

FIG. 1 illustrates steps in the preparation of a neutrophil-specific T7 phage display library. In an exemplary method, neutrophils were isolated from 40 C56 black mice, according to known procedures. RNA was extracted from the neutrophils and converted into cDNA using the OrientExpresscDNA kit from Novagen (U.S. Pat. No. 5,629,179). The neutrophil-derived cDNAs were fused to the coat protein gene in a T7Select Phage-Display System (U.S. Pat. Nos. 5,223,409; 5,403,484; 5,571,698; 5,766,905), and the DNA was packaged into phage particles, creating the library called T7N. The library was then depleted of phage that bound to "background cells", i.e., unstimulated fetal mouse endothelium cells, by three successive steps in which the library was mixed with background cells, and retaining the unbound phage.

To select for neutrophil-specific phage, C57 black mice were injected with anti-Grl to remove neutrophils from the mouse. 24 hours later, the mice were given an IP injection of 0.5 mg/kg lipopolysaccharide (LPS), an inflammatory stimulus that causes upregulation of adhesion molecules on the endothelial lining of blood vessels. These adhesion molecules recruit neutrophils from the blood flow. Three and a half hours later the mice were anesthetized with a 65% dose of ketamine, and twenty minutes later, the mice were injected with $5\times10^9$ pfu of library phage by tail vein, and the phage were allowed to circulate for 10 minutes. The animals were then perfused with 15 mL of PBS, pumped through the left, drained through the right atrium while the heart was still beating, to remove unbound phage in the vasculature.

The lungs, liver, heart, kidneys, brain and leg muscle were harvested, and each organ was minced in 1 mL 10 mM EDTA/PBS, dounce homogenized, and 1 uL of final organ prep was plated for plaque titreing. 10 mL LB with bacterial phage host was added to the remainder of the liver and lungs organ prep to recover the phage that preferentially homed to these organs.

Figure 2A:
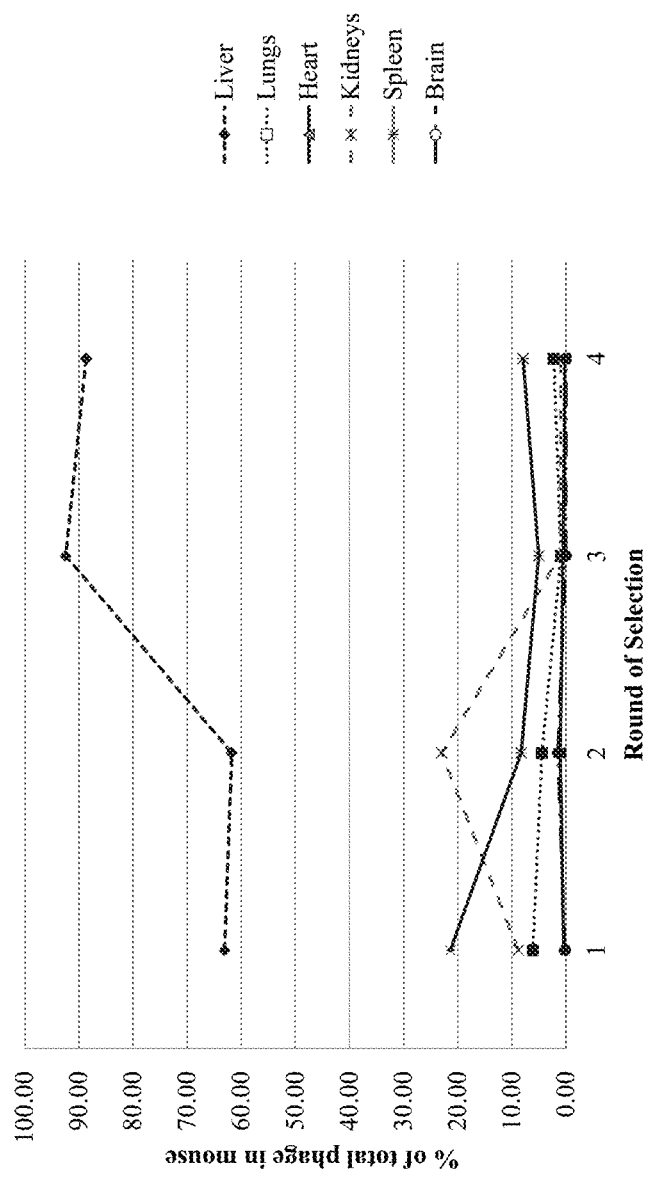
FIGS. 2A and 2B are plots of the distribution of a T7Li phage library to the liver and other organs after 4 rounds of in vivo selection (2A); and the distribution of a T7Lu phage library to the lungs and other tissue after three rounds of in vivo selection (2B)
Figure 2B:
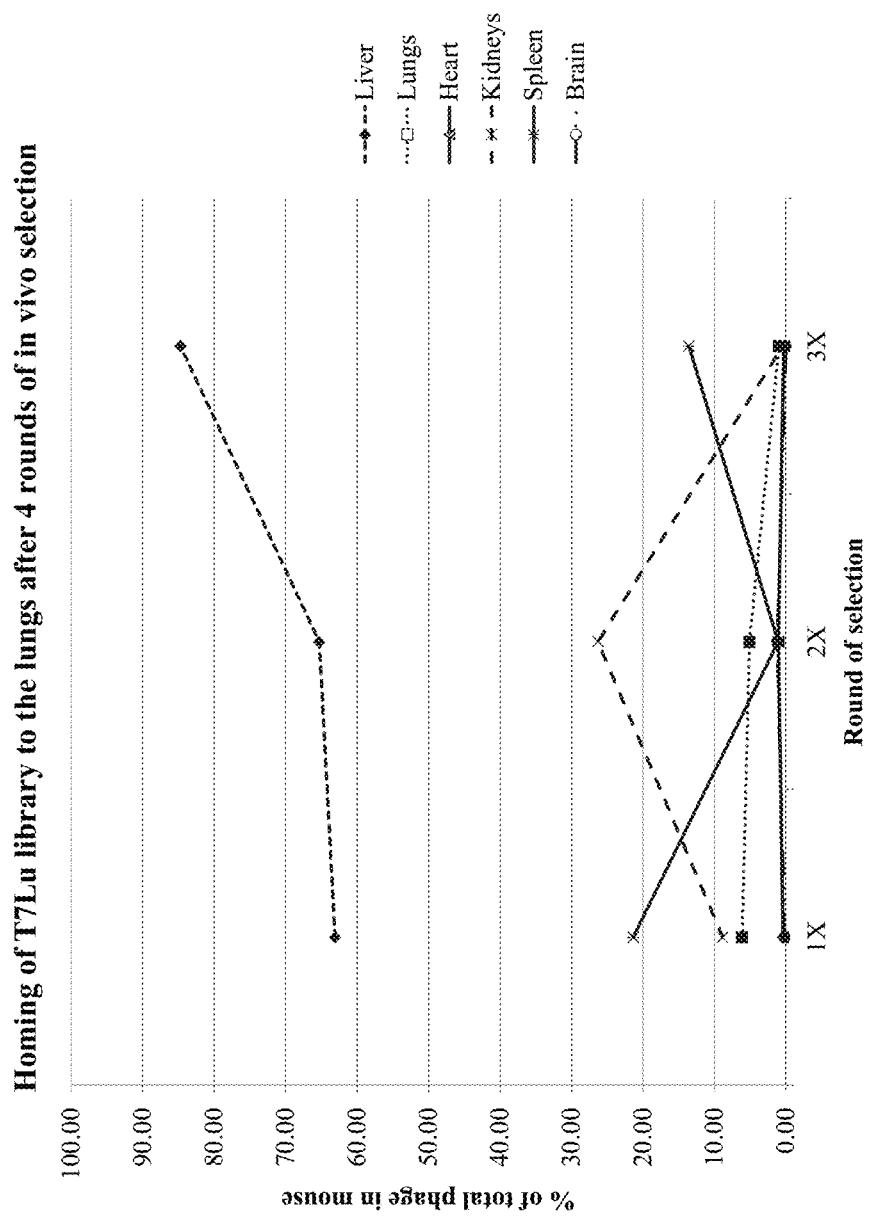

The liver library (T7NLi) was taken through 4 rounds of in vivo selection, but the lung library (T7NLu) only went through 3 rounds, since no enrichment of lung homing phage was seen with further selection, as seen in FIGS. 2A and 2B. Both T7NLi and T7NLu libraries were highly selective for binding to liver, but neither highly selective for lung tissue.

Figure 3A:
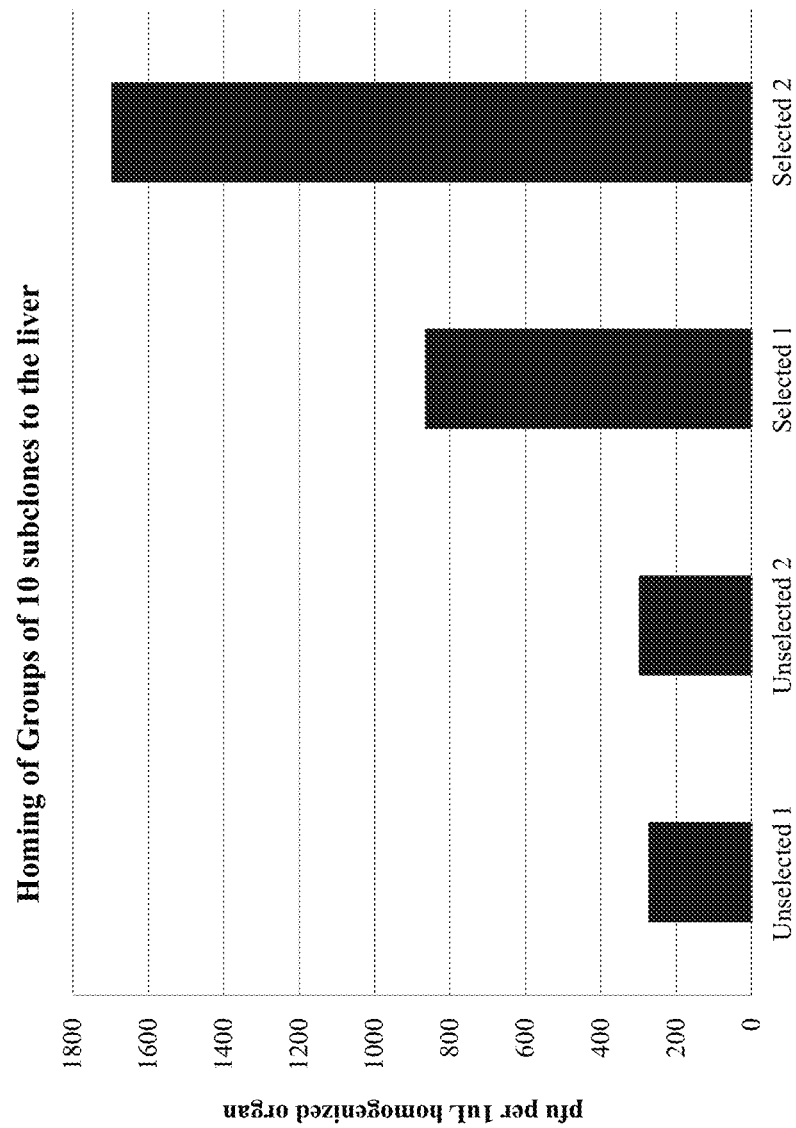
FIGS. 3A and 3B are bar graphs showing the homing of groups of unselected and liver-specific phage display subclones to the liver (3A) and the homing of T7NLi, T7Nlu, and 2-2/2-3 phage subclones into liver, lung, and kidney tissue (3B)
Figure 3B:
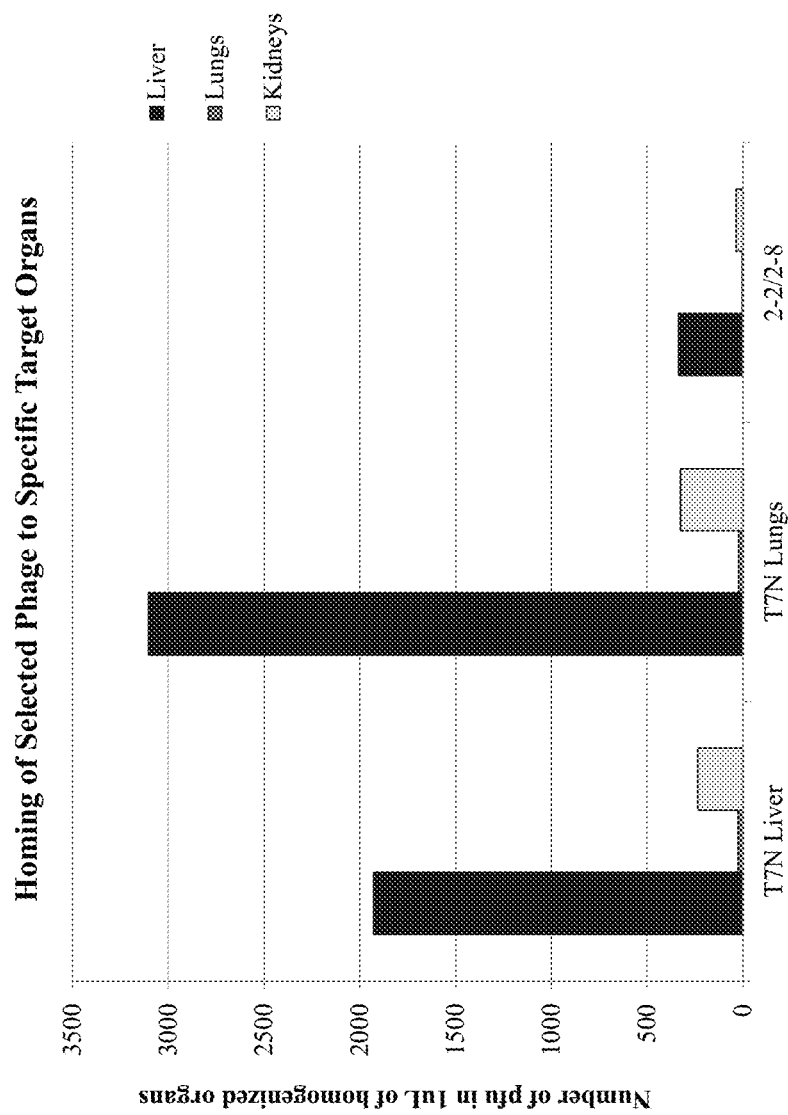

Two groups of 10 plaques from the T7NLi library and two groups of 10 plaques (subclones 1¼-10 and 2½-10) from the original unselected (T7N) library were combined and amplified, then checked for homing to the liver, with the results shown in FIG. 3A. The selected groups of subclones showed significant selective homing to the liver. The T7NLi, T7NLu, and a 50:50 mixture of subclone 2-2 (KKKKKKSWRPPXRN, SEQ ID NO:17) and subclone 2-8 (K2OWXXPPXKFFSPX, SEQ ID NO: 18) from above were also examined for their ability to target liver, lung and kidney tissue, with the results seen in FIG. 3B. Consistent with the results shown in FIGS. 2A and 2B, both the T7NLi and T7NLu libraries were highly selective for binding to liver tissue.

Figure 4A:
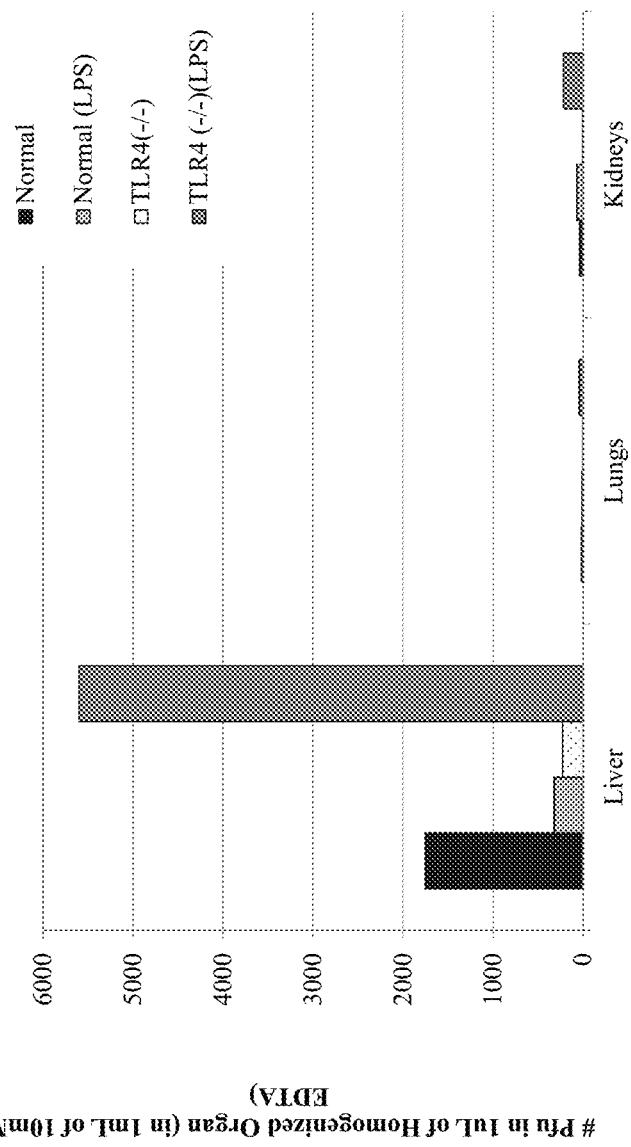
FIGS. 4A and 4B plot the amount of phage captured in liver, lungs, and kidneys in normal and TLR4(−/−) mice with and without LPS pretreatment (4A) and in normal and MyD88 knockout mice (4B)

Example 2: Binding of T7 Liver Phage to Liver in Mice with Immune-Receptor Mutations The inserts in the 10 library phage from each of the selected T7NLi groups were sequenced. One of these, designated subclone 2-2 (KKKKKKSWRPPXRN, SEQ ID NO:17 was selected as a representative liver homing phage. The phage was injected into normal and TLR4(-/-) mice that were either untreated or treated with LPS four hours prior to phage injection. TLR4 (-/-) mice are deficient in Toll-like receptor 4 (TLR4), a receptor that induces the release of critical proinflammatory cytokines that are necessary to activate potent immune responses. The results of the study, plotted in FIG. 4A, show significantly higher binding of the 2-2 T7NLi subclone to the liver of LPS stimulated TLR4(-/-) animals, indicating that in the absence of TLR4, other receptors are upregulated by LPS. Since they are involved in innate immunity, the upregulated receptors may bind to liver-targeting phage, as the data suggests.

Figure 4B:
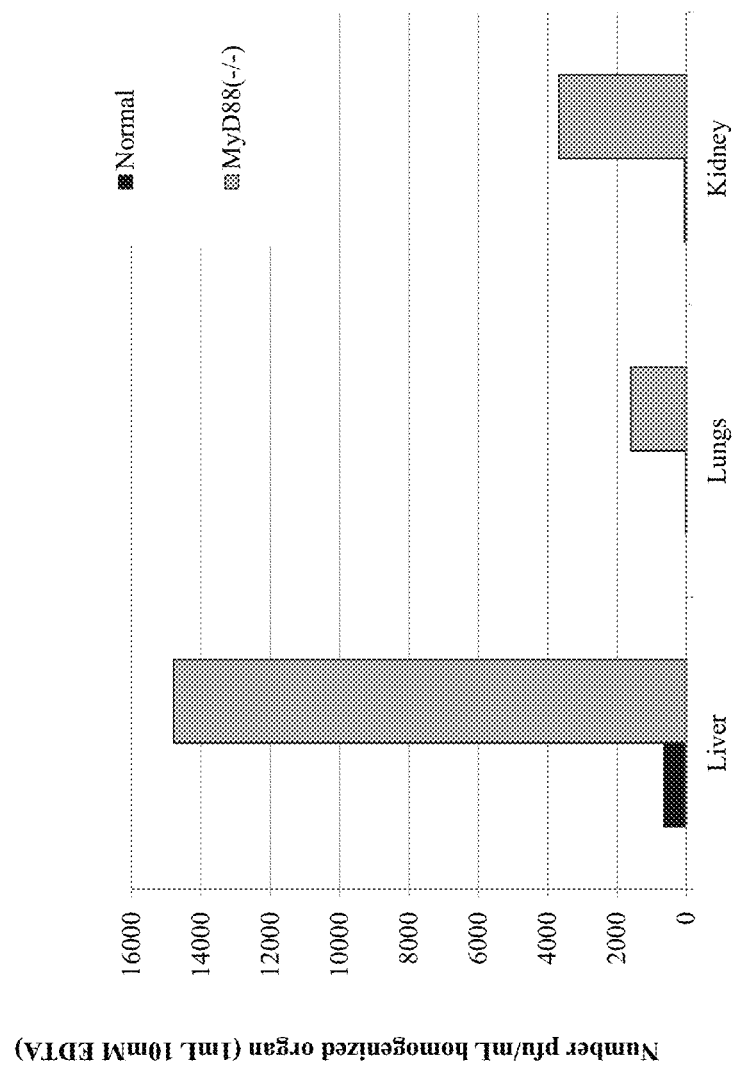

The ability of the 2-2 subclone from T7NLi was also investigated in normal (C57) and MyD88(-/-) mice. The Myd88-deficient allele encodes a deletion of exon 3 of the myeloid differentiation primary response gene 88 locus. Myd88-deficiency is associated with a number of immune system abnormalities, as well as hematopoietic system, molecular signaling, and apoptotic abnormalities. Levels of the 2-2 clone binding to liver, lungs, and kidney in normal and MyD88(-/-) mice are shown in FIG. 4B. As is clear from the results, MyD88 mice overproduce a receptor or other binding protein recognized by the 2-2 subclone.

Example 3: Blocking of Neutrophil Recruitment to the Liver with Selected Peptides The next study examined the ability of various peptides from the T7NLi library to block neutrophil recruitment in the liver. In these studies, the liver was imaged by intravital microscopy, allowing real time observations of neutrophil flow through the liver vasculature. The phage peptides that examined were (1) the full T7NLu library (3× selected), (2) the full T7NLi library (4× selected) and (3) a 50:50 mixture of subclones 2-2 and 2-8 from above.

In each study, a C57 mouse was given a tail vein injection of the phage, and 5 minutes later the animal was anesthetized and the liver video recorded, where the mice were either untreated or given 0.5 mg/kg LPS IP 4 hours before the phage injection. The organs were harvested afterwards without perfusion. A check of homing in selected organs was consistent with earlier results: all three phage samples were selected concentrated in the liver. Surprisingly, the T7NLu library showed higher levels of binding to the liver than the T7NLi library did.

In the video analyses of neutrophil recruitment to the liver by intravital microscopy, the following parameters were measured:
Rolling Velocity in Post Sinusoidal Venules;
Rolling Flux (number of neutrophils to pass a line drawn across a sinusoid within one minute)
Number of Neutrophils adhered in a 100 um segment of a post sinusoidal venule
Number of Neutrophils adhered in the sinusoids in one field of view; and
% Perfusion of sinusoids—measure of liver damage.

Figure 5A:
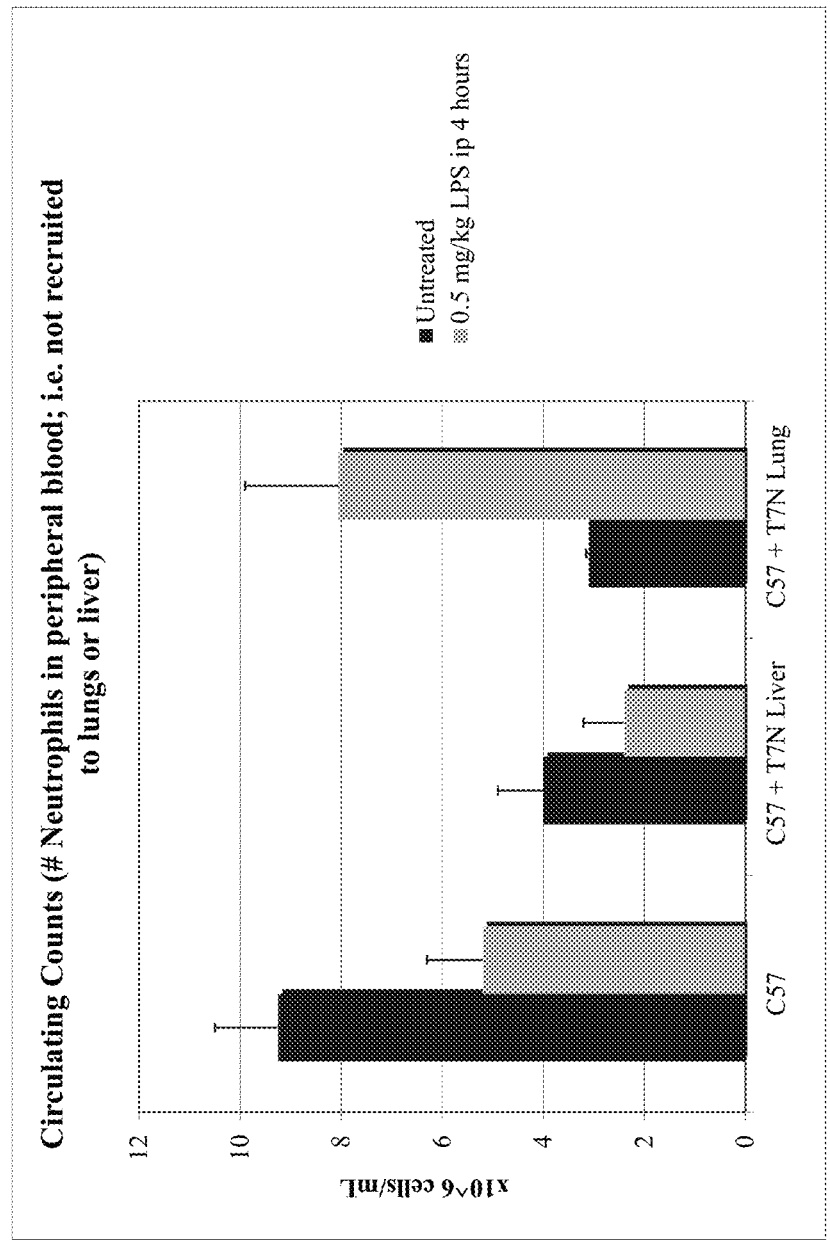
FIGS. 5A and 5B are plots of circulating neutrophil counts measured in C57 mice untreated or treated with T7NLi or T7NLu library phage (5A) and leukocyte rolling flux with C57 mice under the same treatment conditions (5B)

FIG. 5A shows the number of neutrophils in peripheral blood, that is, not recruited to lungs or liver. LPS alone caused a substantial drop in circulating neutrophils, suggesting increased recruitment by the lungs and liver. This effect was largely eliminated in the animals receiving both LPS and the TN7Lu library.

Figure 5B:
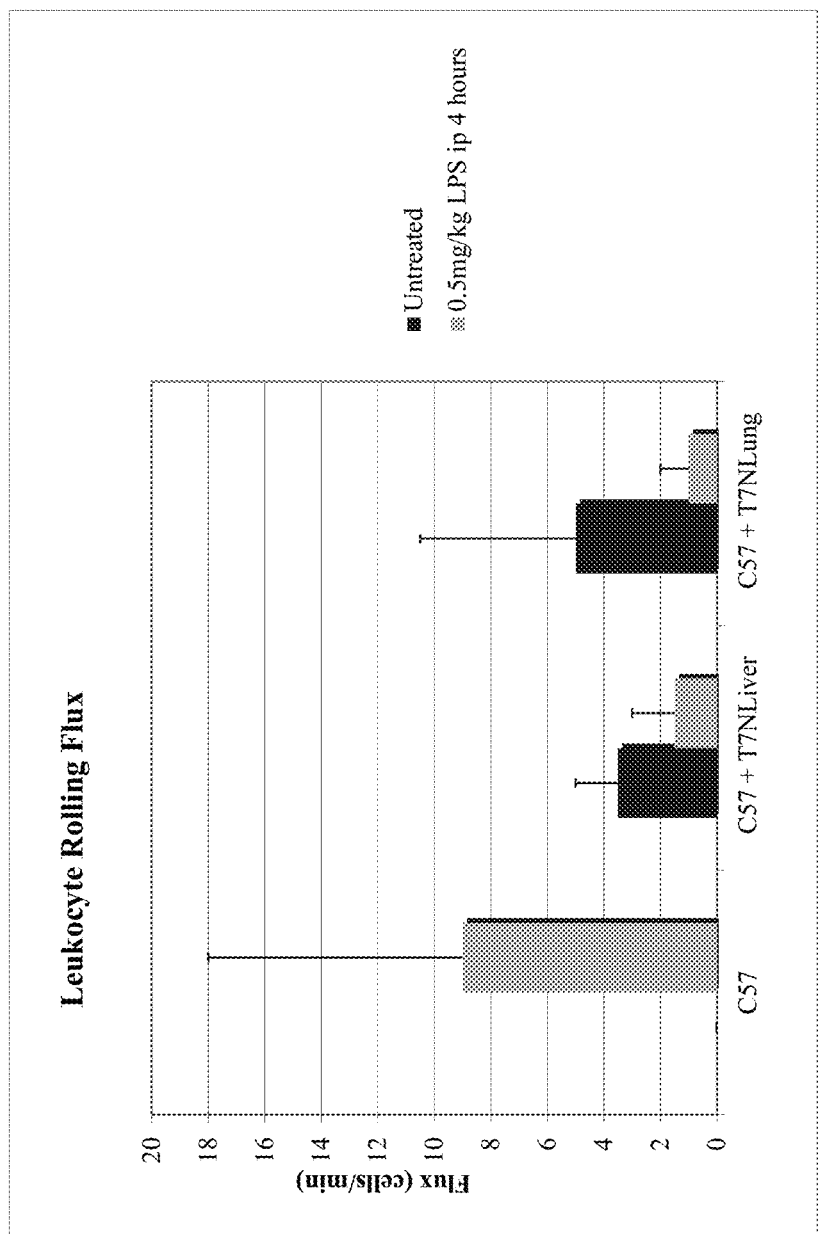

Rolling flux measurements, shown in FIG. 5B, show that both the TN7Li and TN7Lu libraries significantly reduce the flow of neutrophils within a liver sinusoid, indicating less recruitment in sinusoids.

Figure 6A:
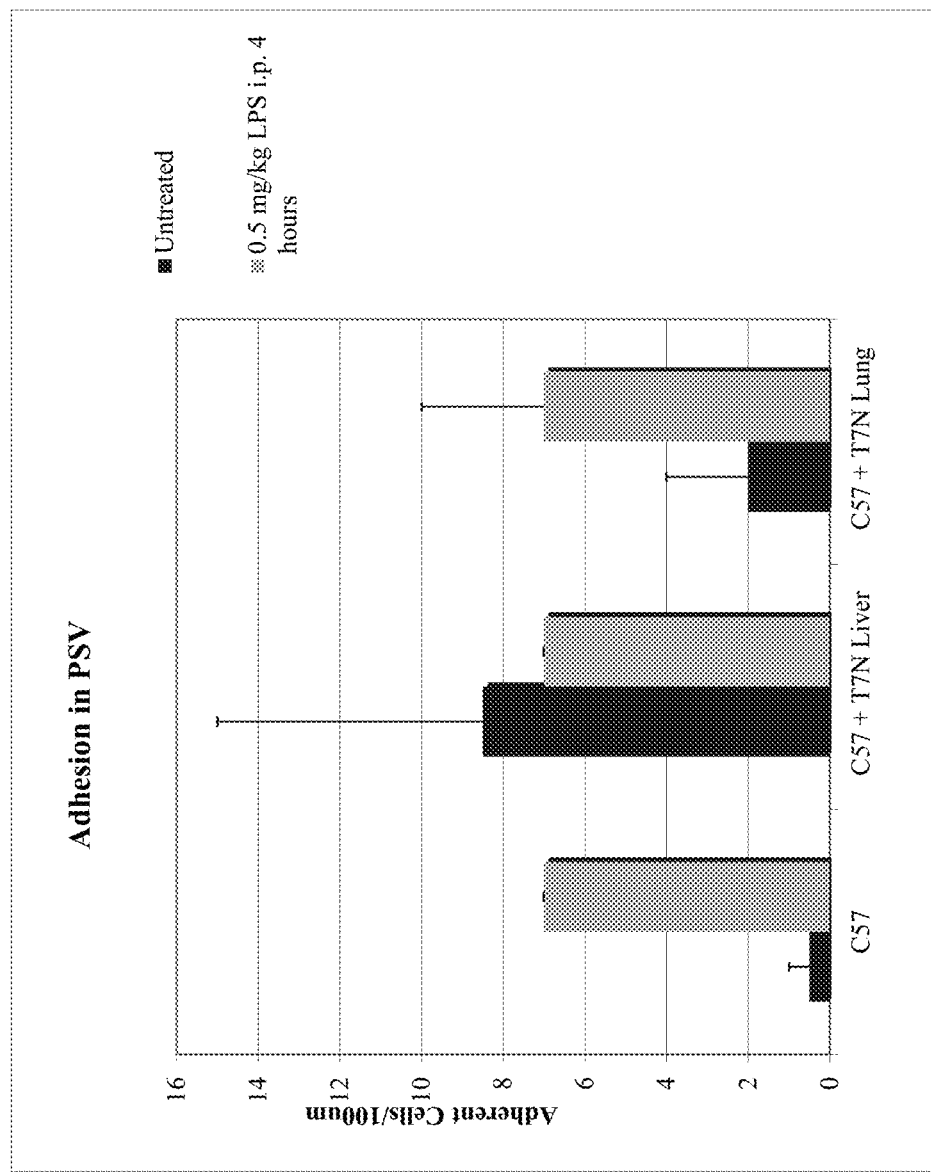
FIGS. 6A and 6B are plots of adhesion in Post Sinusoidal Venules (6A) and % perfusion in C57 mice untreated or treated with T7NLi or T7NLu library phage.

Increased adhesion of neutrophils to a postsinusoidal venule, shown in FIG. 6A, is most likely caused by LPS (a contaminant from having grown the phage in bacterial hosts) present in both the TN7Li T7NLu libraries, indicating that the amount of LPS administered to the mice was higher than intended, and varied depending on the preparation of phage used. This suggests that the ability of the phage to inhibit recruitment in the sinusoids is not hampered by a higher dose of LPS.

Figure 6B:
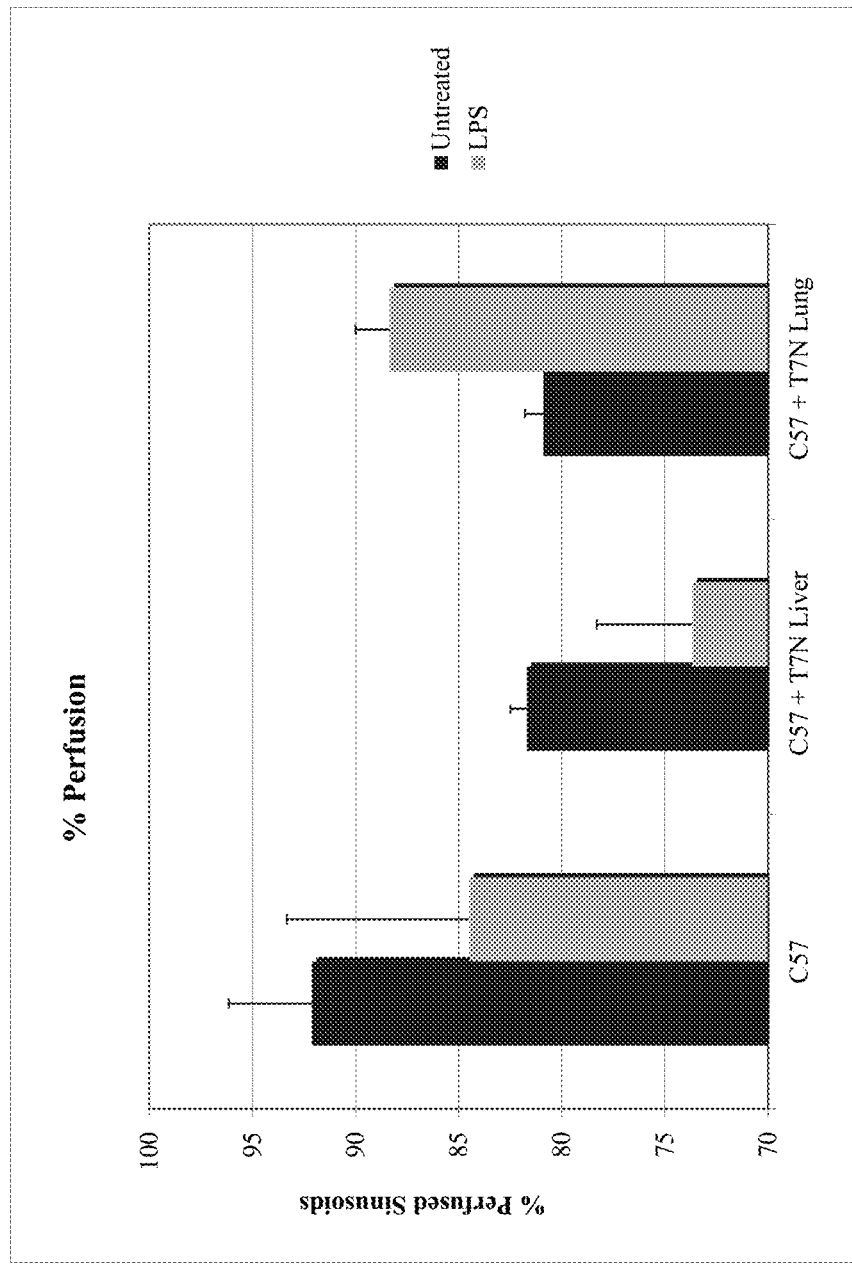

Percent perfusion, is a measure of how much blood flow is present in the liver. Neutrophil recruitment decreases perfusion, resulting in liver damage. The T7NLu library significantly improved perfusion of the liver despite the application of LPS. (FIG. 6B), indicating substantial protection against neutrophil-related damage to the liver.

Example 4: Assessment of Neutrophil Recruitment to the Lungs

Figure 7:
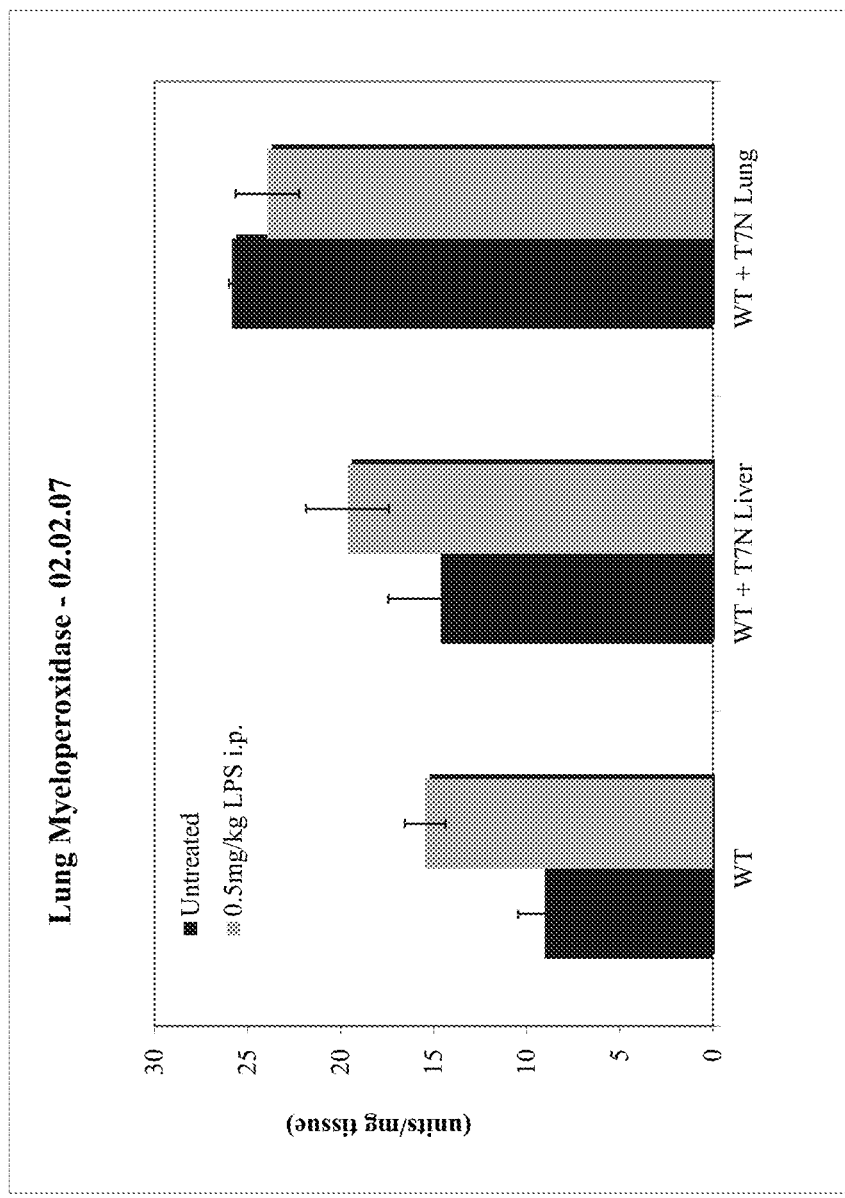
FIG. 7 shows the effect of T7NLi and T7NLu libraries on recruitment of leukocytes in lungs, as measured by leukocyte myeloperoxidase.

Because intravital imaging to the lungs was not available, assessment of neutrophil recruitment to the lungs was performed by measuring the myeloperoxidase, a neutrophil enzyme, present in lung tissue. As seen from the data in FIG. 7, there does not seem to be any reduction in neutrophil with the two phage libraries used. The observed increases may be due to the extra LPS present in the phage preparations.

Example 5: Selection of Phage Clones Effective to Bock Neutrophil Recruitment

Figure 8:
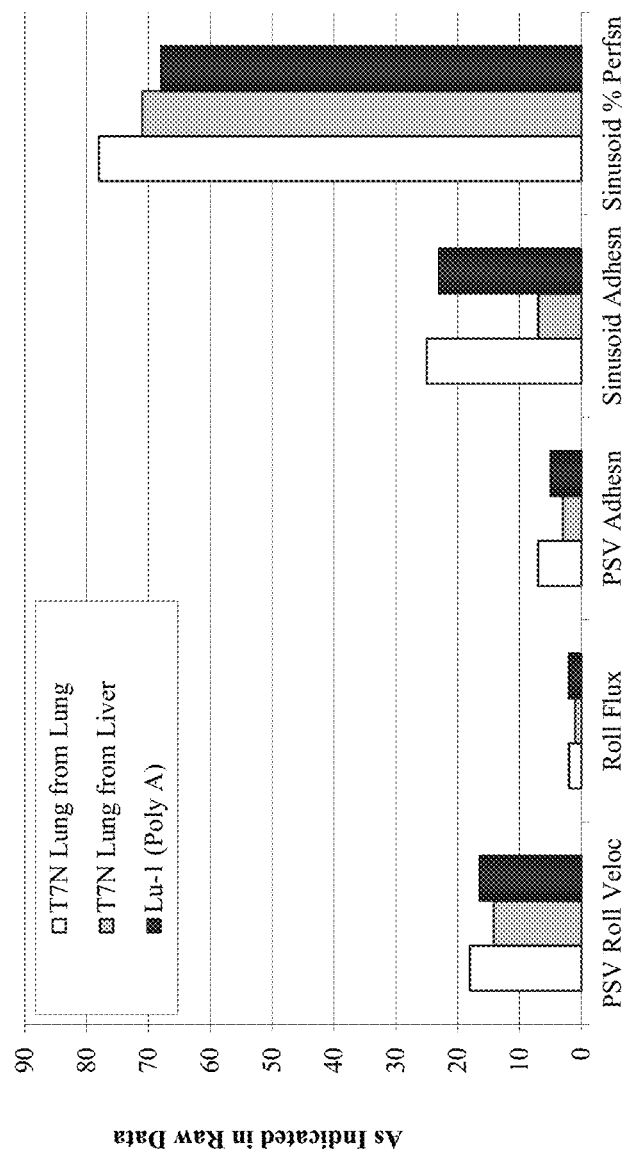
FIG. 8 compares the ability of three phage groups, T7N Lung from Lung, T7N Lung from Liver, and Lu-1 (polyA) to block neutrophil adhesion in mouse liver.

The lungs and livers from a mouse injected with the T7NLu library were homogenized and the phage within them were recovered, creating two new libraries:
T7N Lung→Lung
T7N Lung→Liver These were tested for their abilities to block neutrophil recruitment, with the results shown in FIG. 8. The lung selected phage that went through a round of liver selection appeared to contain phage that were effective in inhibiting adhesion of neutrophils specifically to the endothelium of the liver sinusoids. Single phage clones were picked at random from each of these libraries and grown up for sequencing to try to identify sequences from known human genes. Four of the clones were identified as (1) out of frame product of gene Ube2n; (2) out of frame product of the gene for Clathrin; and (3) out of frame product for the gene of Hemoglobulin.

Another 24 plaques were reamplified, replated and resequenced, and the sequences were matched with the following known human genes: Mkrn1 (8 subclones); Spermidine N1-acetyl transferase; S100a9 (2 subclones); Ube2n (2 subclones); Ngp (3 subclones); Rp134; Chrm 17; Lilrb3; Dnaja2; Hbb-b1; Hba-a1 (2 subclones).

Figure 9:
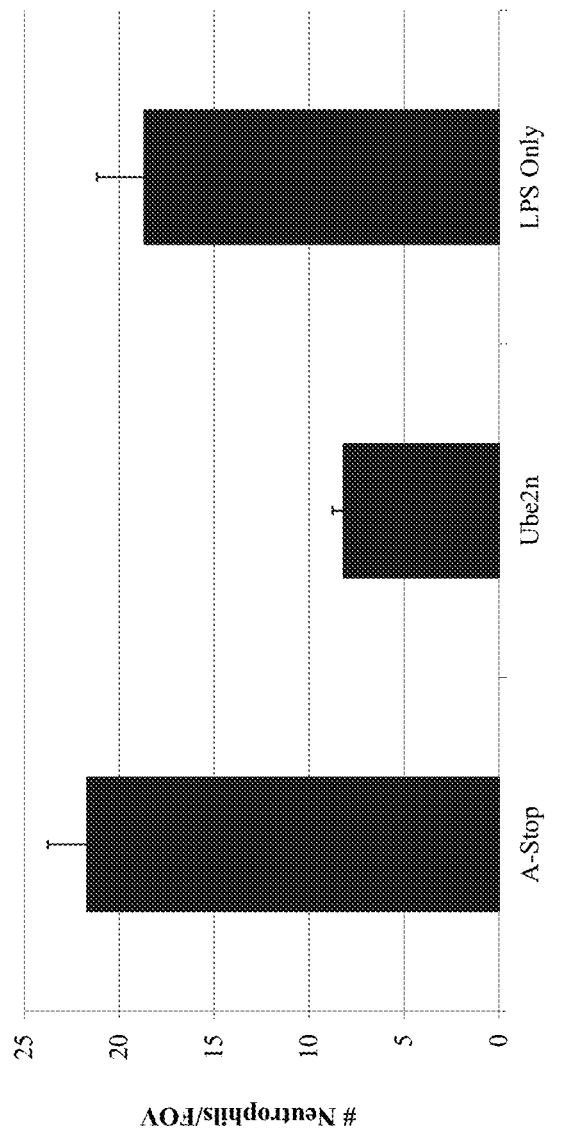
FIG. 9 compares neutrophil adhesion in mouse liver sinusoids after administration of Poly A phage, Ube2n (LSALT) phage, and LPS only.

Since Ube2n is in the group that originally blocked neutrophil adhesion in the liver sinusoids, it was tested against a phage that only displayed an alanine amino acid (A-Stop) and LPS alone. FIG. 9 shows relative neutrophil binding to the liver with these three treatments. From this study, the peptide coded by the out-of frame sequence of Ube2n was identified as a phage subclone that can inhibit adhesion of neutrophils to the liver sinusoids after inflammation induced by LPS. The translated peptide has the sequence LSALTPSPSWLKYKAL (SEQ ID NO: 1), also designated herein as the "LSALT" peptide.

Figure 15A:
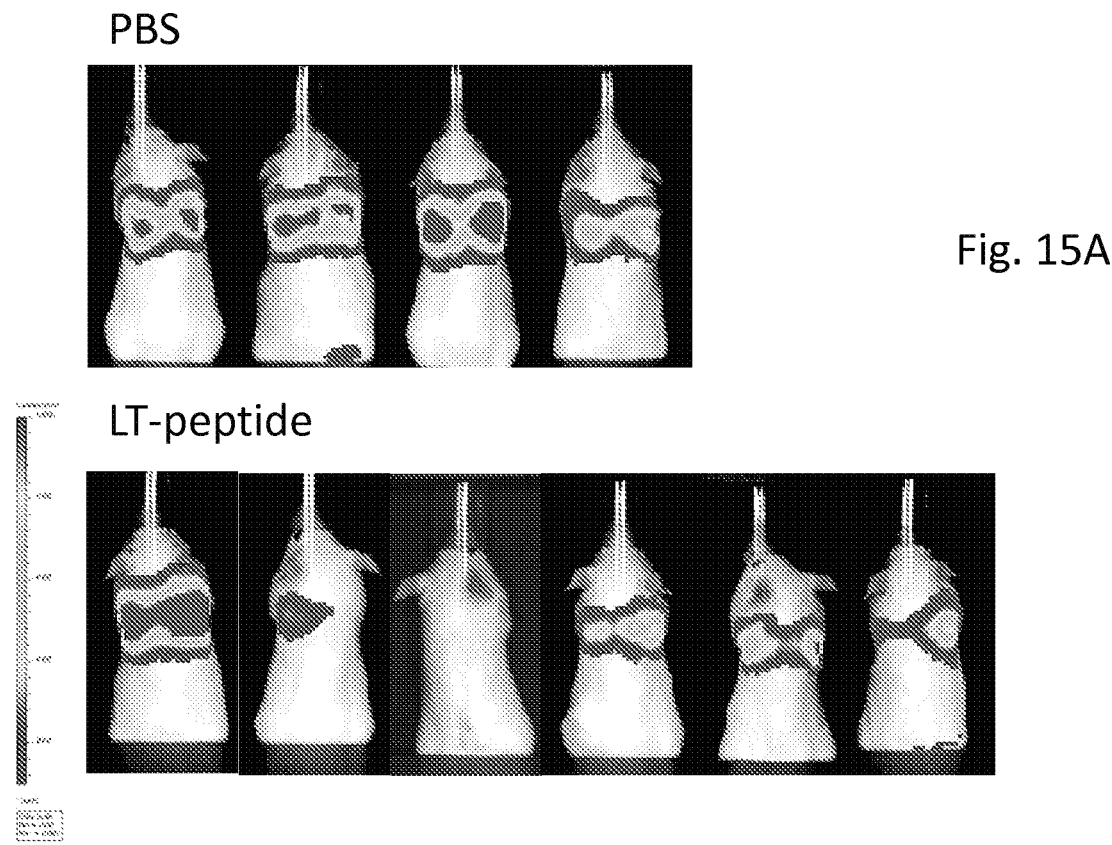
FIGS. 15A and 15B show the effects of LSALT peptide on reducing the number of metastatic lesions in mouse lung after injection of $5 \times 10^5$ 143B human osteosarcoma cells stably expressing luciferase into the tail vein of animals. Representative histological sections (15A) show reduction in metastatic lesions. Similarly, quantification of the number of metastatic lesions for all lobes of the right and left lungs in five non-sequential histological sections is shown graphically in 15B.
Figure 15B:
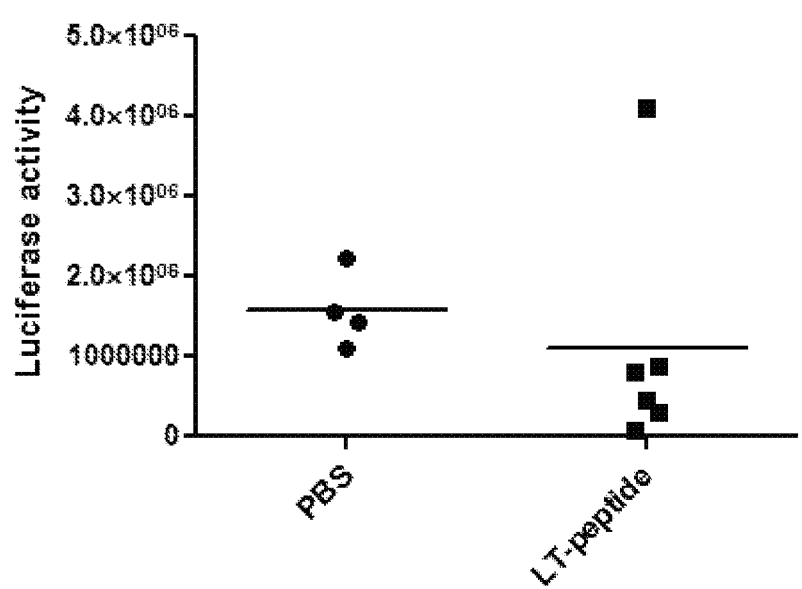

Example 6: Assessment of Peptide Efficacy on Metastasis of 143B Human Osteosarcoma Cells in Mouse Model for Metastasis $5 \times 10^5$ 143B human osteosarcoma cells stably expressing luciferase were injected into the tail vein of animals 5 mins after IV delivery of PBS or LSALT-peptide. Animals were sacrificed after 3 weeks. Lungs were then harvested, fixed in formalin, and embedded in paraffin. FIG. 15A shows representative histological sections of the lobes of the right lung of animals. Metastatic lesions were visualized by staining human 143B osteosarcoma cells with anti-human nucleolin (brown). FIG. 15B provides a graph shows quantification of the number of metastatic lesions for all lobes of the right and left lungs in five non-sequential histological sections. PBS n=4. LSALT-peptide n=6.

In a similar model, $5 \times 10^5$ 143B human osteosarcoma cells stably expressing luciferase were injected into the tail vein of animals 5 mins after IV delivery of PBS or LSALT-peptide. Animals were imaged weekly using bioluminescence imaging (Xenogen, IVIS 200).

Figure 16A:
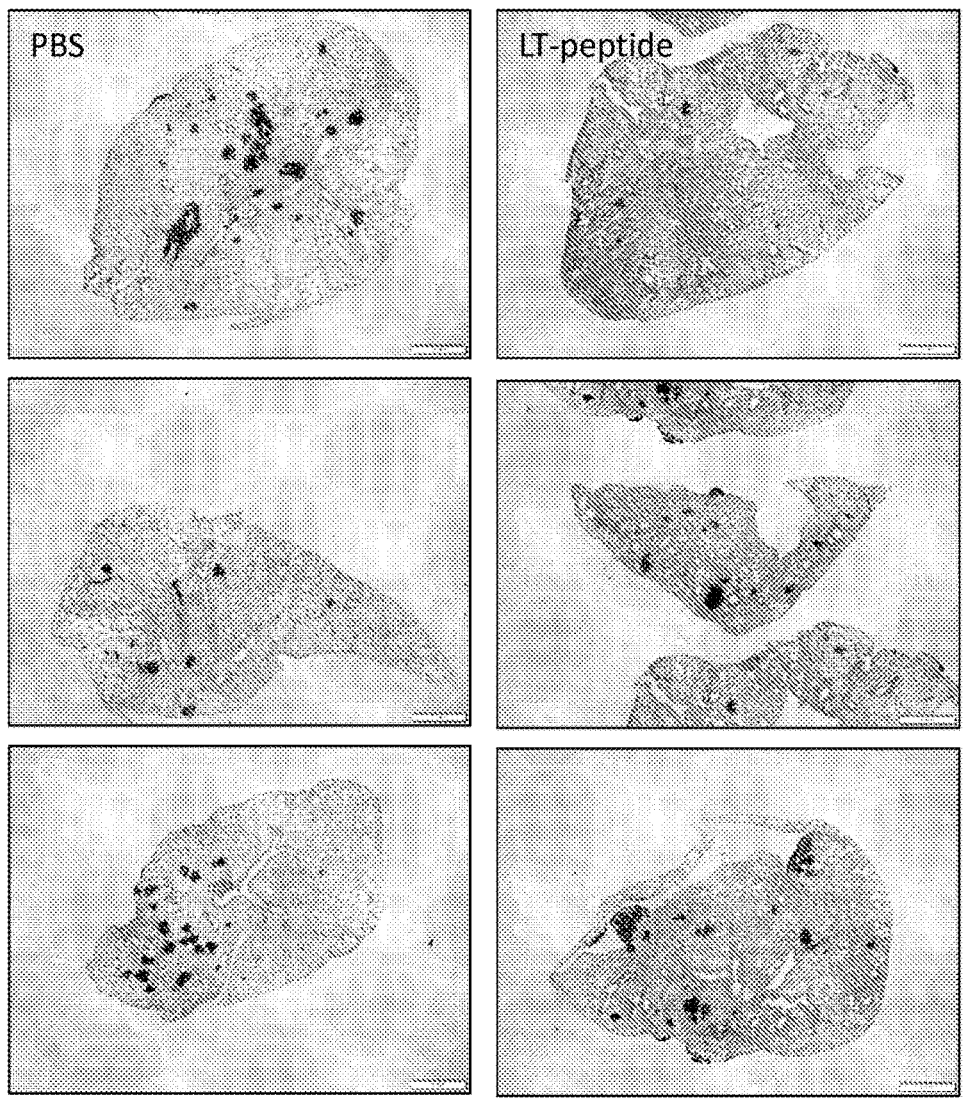
FIGS. 16A and 16B show the effects of LSALT peptide on reducing metastatic burden in mouse liver after injection of $5 \times 10^5$ 143B human osteosarcoma cells stably expressing luciferase into the tail vein of animals. Representative bioluminescence images of animals 3 weeks post injection (16A) shows reduction in bioluminescence. Quantification of luciferase activity to show metastatic burden in these animals is shown graphically in FIG. 16B.
Figure 16B:
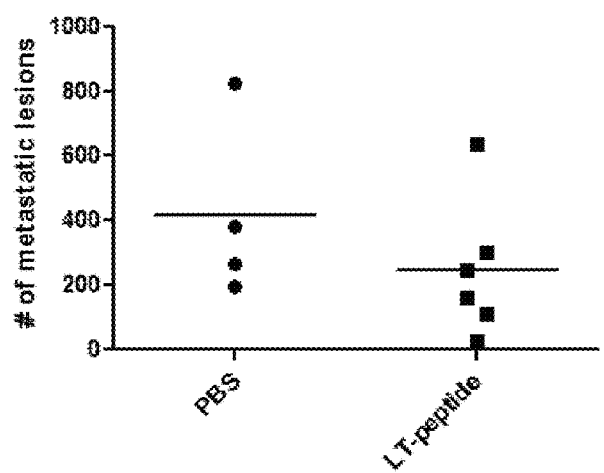

FIG. 16A shows bioluminescence images of animals 3 weeks post-injection (30 sec. exposure time). FIG. 16B provides a graph shows quantification of luciferase activity (metastatic burden) in animals in A. PBS n=4. LSALT-peptide n=6.

These results show that the LSALT peptide also blocks the metastatic spread of an osteosarcoma cell line to the liver. This is specifically germane since once metastatic this disease is very aggressive and the lung is a preferred organ for metastases.

Example 7: Assessment of Peptide Efficacy on Sepsis

An intoxication model of sepsis was used to assess peptide efficacy on sepsis. In intoxication models, mice are challenged with a noninfectious, proinflammatory compound, such as LPS or killed bacteria. In the present study, protocols were used that followed Andonegui G, et al., J Clin Invest. 2009 July; 119(7):1921-30; and Yipp B G, et al. J Immunol. 2002 May 1; 168(9):4650-8.

Briefly, purified LPS isolated from *E. Coli* was used to initiate endotoxemia response in BALB/c mice 6-8 weeks old. Mice were injected with LSALT bacteriophage that contain lethal amounts of LPS endotoxin.

Figure 17A:
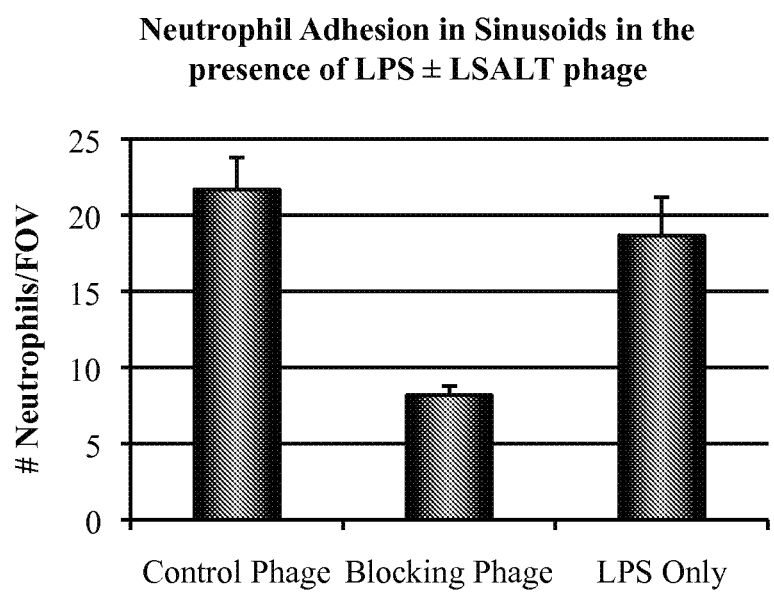
FIGS. 17A and 17B show the effects of LSALT peptide in a mouse model of sepsis. Neutrophil adhesion in sinusoids was evaluated in the presence of control-bacteriophage/LPS, LSALT-bacteriophage/LPS, and LPS only (FIG. 17A). Injection with LSALT-bacteriophage had a protective effect on LPS-induced acute inflammation (in 4 of 5 mice) (FIG. 17B).
Figure 17B:
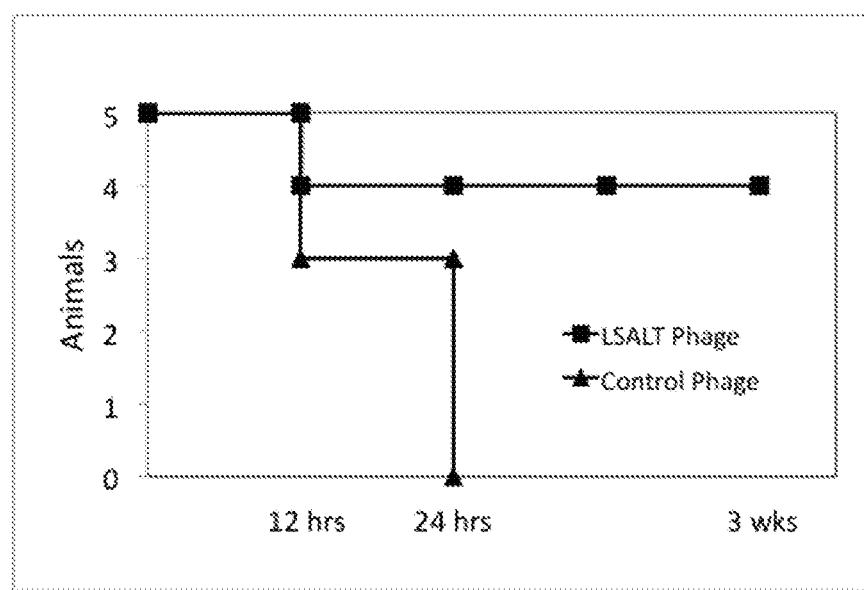

When the animals started to show signs of distress they were sacrificed by euthanasia. All mice treated in this group (5 out of 5) had to be sacrificed due to a septic response. Neutrophil adhesion in sinusoids was evaluated in the presence of control-bacteriophage/LPS, LSALT-bacteriophage/LPS, and LPS only demonstrating a protective effect of the LSALT-bacteriophage (FIG. 17A). Mice injected with the LSALT-bacteriophage demonstrated a protective effect of the LSALT-bacteriophage compared to control. All but one animal survived the dosing (1 out of 5) (FIG. 17B).

It will be appreciated how various changes and modifications may be made without departing from the invention, as embodied in the claims below.

We claim:

1. A method of inhibiting leukocyte-recruitment in a patient in need thereof by administering to the patient a pharmaceutically effective amount of an isolated peptide containing the sequence LSALTPSPSWLKYKAL (SEQ ID NO: 1).

2. The method of claim 1 wherein the isolated peptide further comprises 1, 2, 3, 4, or 5 amino acid residues at the N-terminus and C-terminus of LSALTPSPSWLKYKAL (SEQ ID NO: 1).

3. The method of claim 1 wherein the isolated peptide is modified by pegylation, acetylation, glycosylation, biotinylation, methylation or acetylation.

4. The method of claim 1 wherein the isolated peptide is administered at a dosage between about 0.01 mg/kg to 100 mg/kg.

* * * * *

SEQUENCE LISTING

```
<160> NUMBER OF SEQ ID NOS: 36

<210> SEQ ID NO 1
<211> LENGTH: 16
<212> TYPE: PRT
<213> ORGANISM: Homo sapiens

<400> SEQUENCE: 1
```

```
Leu Ser Ala Leu Thr Pro Ser Pro Ser Trp Leu Lys Tyr Lys Ala Leu
1               5                   10                  15
```

<210> SEQ ID NO 2
<211> LENGTH: 13
<212> TYPE: PRT
<213> ORGANISM: Homo sapiens

<400> SEQUENCE: 2

```
Cys Gly Phe Glu Cys Val Arg Gln Cys Pro Glu Arg Cys
1               5                   10
```

<210> SEQ ID NO 3
<211> LENGTH: 8
<212> TYPE: PRT
<213> ORGANISM: Homo sapiens

<400> SEQUENCE: 3

```
Cys Gly Phe Glu Leu Glu Thr Cys
1               5
```

<210> SEQ ID NO 4
<211> LENGTH: 17
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is any naturally-occurring amino acid,
      unconventional amino acid or amino acid analog

<400> SEQUENCE: 4

```
Xaa Leu Ser Ala Leu Thr Pro Ser Pro Ser Trp Leu Lys Tyr Lys Ala
1               5                   10                  15

Leu
```

<210> SEQ ID NO 5
<211> LENGTH: 18
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: X is any naturally-occurring amino acid,
      unconventional amino acid or amino acid analog

<400> SEQUENCE: 5

```
Xaa Xaa Leu Ser Ala Leu Thr Pro Ser Pro Ser Trp Leu Lys Tyr Lys
1               5                   10                  15

Ala Leu
```

<210> SEQ ID NO 6
<211> LENGTH: 19
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X is any naturally-occurring amino acid,
      unconventional amino acid or amino acid analog

<400> SEQUENCE: 6

```
Xaa Xaa Xaa Leu Ser Ala Leu Thr Pro Ser Pro Ser Trp Leu Lys Tyr
1               5                   10                  15

Lys Ala Leu
```

<210> SEQ ID NO 7
<211> LENGTH: 20
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: X is any naturally-occurring amino acid,
      unconventional amino acid or amino acid analog

<400> SEQUENCE: 7

Xaa Xaa Xaa Xaa Leu Ser Ala Leu Thr Pro Ser Pro Ser Trp Leu Lys
1               5                   10                  15

Tyr Lys Ala Leu
            20

<210> SEQ ID NO 8
<211> LENGTH: 17
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is any naturally-occurring amino acid,
      unconventional amino acid or amino acid analog
<220> FEATURE:
<221> NAME/KEY: misc_feature
<222> LOCATION: (17)..(17)
<223> OTHER INFORMATION: Xaa can be any naturally occurring amino acid

<400> SEQUENCE: 8

Leu Ser Ala Leu Thr Pro Ser Pro Ser Trp Leu Lys Tyr Lys Ala Leu
1               5                   10                  15

Xaa

<210> SEQ ID NO 9
<211> LENGTH: 18
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: X is any naturally-occurring amino acid,
      unconventional amino acid or amino acid analog
<220> FEATURE:
<221> NAME/KEY: misc_feature
<222> LOCATION: (17)..(18)
<223> OTHER INFORMATION: Xaa can be any naturally occurring amino acid

<400> SEQUENCE: 9

Leu Ser Ala Leu Thr Pro Ser Pro Ser Trp Leu Lys Tyr Lys Ala Leu
1               5                   10                  15

Xaa Xaa

<210> SEQ ID NO 10
<211> LENGTH: 19
<212> TYPE: PRT
<213> ORGANISM: Homo sapiens
<220> FEATURE:
<221> NAME/KEY: misc_feature
<222> LOCATION: (17)..(19)
<223> OTHER INFORMATION: Xaa can be any naturally occurring amino acid

<400> SEQUENCE: 10

Leu Ser Ala Leu Thr Pro Ser Pro Ser Trp Leu Lys Tyr Lys Ala Leu
1               5                   10                  15

Xaa Xaa Xaa

```
<210> SEQ ID NO 11
<211> LENGTH: 20
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X is any naturally-occurring amino acid,
      unconventional amino acid or amino acid analog
<220> FEATURE:
<221> NAME/KEY: misc_feature
<222> LOCATION: (17)..(20)
<223> OTHER INFORMATION: Xaa can be any naturally occurring amino acid

<400> SEQUENCE: 11

Leu Ser Ala Leu Thr Pro Ser Pro Ser Trp Leu Lys Tyr Lys Ala Leu
1               5                   10                  15

Xaa Xaa Xaa Xaa
            20

<210> SEQ ID NO 12
<211> LENGTH: 18
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (18)..(18)
<223> OTHER INFORMATION: X is any naturally-occurring amino acid,
      unconventional amino acid or amino acid analog

<400> SEQUENCE: 12

Xaa Leu Ser Ala Leu Thr Pro Ser Pro Ser Trp Leu Lys Tyr Lys Ala
1               5                   10                  15

Leu Xaa

<210> SEQ ID NO 13
<211> LENGTH: 19
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (18)..(19)
<223> OTHER INFORMATION: X is any naturally-occurring amino acid,
      unconventional amino acid or amino acid analog

<400> SEQUENCE: 13

Xaa Leu Ser Ala Leu Thr Pro Ser Pro Ser Trp Leu Lys Tyr Lys Ala
1               5                   10                  15

Leu Xaa Xaa

<210> SEQ ID NO 14
<211> LENGTH: 20
<212> TYPE: PRT
<213> ORGANISM: Homo sapiens
<220> FEATURE:
<221> NAME/KEY: MISC_FEATURE
<222> LOCATION: (1)..(1)
```

```
<223> OTHER INFORMATION: X is any naturally-occurring amino acid,
      unconventional amino acid or amino acid analog
<220> FEATURE:
<221> NAME/KEY: MISC_FEATURE
<222> LOCATION: (18)..(20)
<223> OTHER INFORMATION: X is any naturally-occurring amino acid,
      unconventional amino acid or amino acid analog

<400> SEQUENCE: 14

Xaa Leu Ser Ala Leu Thr Pro Ser Pro Ser Trp Leu Lys Tyr Lys Ala
1               5                   10                  15

Leu Xaa Xaa Xaa
            20

<210> SEQ ID NO 15
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (18)..(21)
<223> OTHER INFORMATION: X is any naturally-occurring amino acid,
      unconventional amino acid or amino acid analog

<400> SEQUENCE: 15

Xaa Leu Ser Ala Leu Thr Pro Ser Pro Ser Trp Leu Lys Tyr Lys Ala
1               5                   10                  15

Leu Xaa Xaa Xaa Xaa
            20

<210> SEQ ID NO 16
<211> LENGTH: 22
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (18)..(22)
<223> OTHER INFORMATION: X is any naturally-occurring amino acid,
      unconventional amino acid or amino acid analog

<400> SEQUENCE: 16

Xaa Leu Ser Ala Leu Thr Pro Ser Pro Ser Trp Leu Lys Tyr Lys Ala
1               5                   10                  15

Leu Xaa Xaa Xaa Xaa Xaa
            20

<210> SEQ ID NO 17
<211> LENGTH: 19
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (19)..(19)
<223> OTHER INFORMATION: X is any naturally-occurring amino acid,
      unconventional amino acid or amino acid analog
```

<400> SEQUENCE: 17

Xaa Xaa Leu Ser Ala Leu Thr Pro Ser Pro Ser Trp Leu Lys Tyr Lys
1               5                   10                  15

Ala Leu Xaa

<210> SEQ ID NO 18
<211> LENGTH: 19
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (18)..(19)
<223> OTHER INFORMATION: X is any naturally-occurring amino acid,
      unconventional amino acid or amino acid analog

<400> SEQUENCE: 18

Xaa Xaa Leu Ser Ala Leu Thr Pro Ser Pro Ser Trp Leu Lys Tyr Lys
1               5                   10                  15

Ala Xaa Xaa

<210> SEQ ID NO 19
<211> LENGTH: 21
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (19)..(20)
<223> OTHER INFORMATION: X is any naturally-occurring amino acid,
      unconventional amino acid or amino acid analog
<220> FEATURE:
<221> NAME/KEY: misc_feature
<222> LOCATION: (21)..(21)
<223> OTHER INFORMATION: Xaa can be any naturally occurring amino acid

<400> SEQUENCE: 19

Xaa Xaa Leu Ser Ala Leu Thr Pro Ser Pro Ser Trp Leu Lys Tyr Lys
1               5                   10                  15

Ala Leu Xaa Xaa Xaa
            20

<210> SEQ ID NO 20
<211> LENGTH: 22
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (19)..(22)
<223> OTHER INFORMATION: X is any naturally-occurring amino acid,
      unconventional amino acid or amino acid analog

<400> SEQUENCE: 20

Xaa Xaa Leu Ser Ala Leu Thr Pro Ser Pro Ser Trp Leu Lys Tyr Lys
1               5                   10                  15

Ala Leu Xaa Xaa Xaa Xaa
            20

<210> SEQ ID NO 21
<211> LENGTH: 23
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (19)..(23)
<223> OTHER INFORMATION: X is any naturally-occurring amino acid,
      unconventional amino acid or amino acid analog

<400> SEQUENCE: 21

Xaa Xaa Leu Ser Ala Leu Thr Pro Ser Pro Ser Trp Leu Lys Tyr Lys
1               5                   10                  15

Ala Leu Xaa Xaa Xaa Xaa Xaa
            20

<210> SEQ ID NO 22
<211> LENGTH: 20
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (20)..(20)
<223> OTHER INFORMATION: X is any naturally-occurring amino acid,
      unconventional amino acid or amino acid analog

<400> SEQUENCE: 22

Xaa Xaa Xaa Leu Ser Ala Leu Thr Pro Ser Pro Ser Trp Leu Lys Tyr
1               5                   10                  15

Lys Ala Leu Xaa
            20

<210> SEQ ID NO 23
<211> LENGTH: 21
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (20)..(21)
<223> OTHER INFORMATION: X is any naturally-occurring amino acid,
      unconventional amino acid or amino acid analog

<400> SEQUENCE: 23

Xaa Xaa Xaa Leu Ser Ala Leu Thr Pro Ser Pro Ser Trp Leu Lys Tyr
1               5                   10                  15

Lys Ala Leu Xaa Xaa
            20

<210> SEQ ID NO 24
<211> LENGTH: 22

```
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (20)..(22)
<223> OTHER INFORMATION: X is any naturally-occurring amino acid,
      unconventional amino acid or amino acid analog

<400> SEQUENCE: 24

Xaa Xaa Xaa Leu Ser Ala Leu Thr Pro Ser Pro Ser Trp Leu Lys Tyr
1               5                   10                  15

Lys Ala Leu Xaa Xaa Xaa
            20

<210> SEQ ID NO 25
<211> LENGTH: 23
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (20)..(23)
<223> OTHER INFORMATION: X is any naturally-occurring amino acid,
      unconventional amino acid or amino acid analog

<400> SEQUENCE: 25

Xaa Xaa Xaa Leu Ser Ala Leu Thr Pro Ser Pro Ser Trp Leu Lys Tyr
1               5                   10                  15

Lys Ala Leu Xaa Xaa Xaa Xaa
            20

<210> SEQ ID NO 26
<211> LENGTH: 24
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (20)..(24)
<223> OTHER INFORMATION: X is any naturally-occurring amino acid,
      unconventional amino acid or amino acid analog

<400> SEQUENCE: 26

Xaa Xaa Xaa Leu Ser Ala Leu Thr Pro Ser Pro Ser Trp Leu Lys Tyr
1               5                   10                  15

Lys Ala Leu Xaa Xaa Xaa Xaa Xaa
            20

<210> SEQ ID NO 27
<211> LENGTH: 21
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: X is any naturally-occurring amino acid,
      unconventional amino acid or amino acid analog
```

-continued

```
<220> FEATURE:
<221> NAME/KEY: MISC_FEATURE
<222> LOCATION: (21)..(21)
<223> OTHER INFORMATION: X is any naturally-occurring amino acid,
      unconventional amino acid or amino acid analog

<400> SEQUENCE: 27

Xaa Xaa Xaa Xaa Leu Ser Ala Leu Thr Pro Ser Pro Ser Trp Leu Lys
1               5                   10                  15

Tyr Lys Ala Leu Xaa
            20

<210> SEQ ID NO 28
<211> LENGTH: 22
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (21)..(22)
<223> OTHER INFORMATION: X is any naturally-occurring amino acid,
      unconventional amino acid or amino acid analog

<400> SEQUENCE: 28

Xaa Xaa Xaa Xaa Leu Ser Ala Leu Thr Pro Ser Pro Ser Trp Leu Lys
1               5                   10                  15

Tyr Lys Ala Leu Xaa Xaa
            20

<210> SEQ ID NO 29
<211> LENGTH: 23
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (21)..(23)
<223> OTHER INFORMATION: X is any naturally-occurring amino acid,
      unconventional amino acid or amino acid analog

<400> SEQUENCE: 29

Xaa Xaa Xaa Xaa Leu Ser Ala Leu Thr Pro Ser Pro Ser Trp Leu Lys
1               5                   10                  15

Tyr Lys Ala Leu Xaa Xaa Xaa
            20

<210> SEQ ID NO 30
<211> LENGTH: 24
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (21)..(24)
<223> OTHER INFORMATION: X is any naturally-occurring amino acid,
      unconventional amino acid or amino acid analog

<400> SEQUENCE: 30
```

Xaa Xaa Xaa Xaa Leu Ser Ala Leu Thr Pro Ser Pro Ser Trp Leu Lys
1               5                   10                  15

Tyr Lys Ala Leu Xaa Xaa Xaa Xaa
            20

<210> SEQ ID NO 31
<211> LENGTH: 25
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (21)..(25)
<223> OTHER INFORMATION: X is any naturally-occurring amino acid,
      unconventional amino acid or amino acid analog

<400> SEQUENCE: 31

Xaa Xaa Xaa Xaa Leu Ser Ala Leu Thr Pro Ser Pro Ser Trp Leu Lys
1               5                   10                  15

Tyr Lys Ala Leu Xaa Xaa Xaa Xaa Xaa
            20                  25

<210> SEQ ID NO 32
<211> LENGTH: 22
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (22)..(22)
<223> OTHER INFORMATION: X is any naturally-occurring amino acid,
      unconventional amino acid or amino acid analog

<400> SEQUENCE: 32

Xaa Xaa Xaa Xaa Xaa Leu Ser Ala Leu Thr Pro Ser Pro Ser Trp Leu
1               5                   10                  15

Lys Tyr Lys Ala Leu Xaa
            20

<210> SEQ ID NO 33
<211> LENGTH: 23
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: X is any naturally-occurring amino acid,
      unconventional amino acid or amino acid analog
<220> FEATURE:
<221> NAME/KEY: MISC_FEATURE
<222> LOCATION: (22)..(23)
<223> OTHER INFORMATION: X is any naturally-occurring amino acid,
      unconventional amino acid or amino acid analog

<400> SEQUENCE: 33

Xaa Xaa Xaa Xaa Xaa Leu Ser Ala Leu Thr Pro Ser Pro Ser Trp Leu
1               5                   10                  15

Lys Tyr Lys Ala Leu Xaa Xaa
            20

<210> SEQ ID NO 34
<211> LENGTH: 24
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: X is any naturally-occurring amino acid, unconventional amino acid or amino acid analog
<220> FEATURE:
<221> NAME/KEY: MISC_FEATURE
<222> LOCATION: (22)..(24)
<223> OTHER INFORMATION: X is any naturally-occurring amino acid, unconventional amino acid or amino acid analog

<400> SEQUENCE: 34

Xaa Xaa Xaa Xaa Xaa Leu Ser Ala Leu Thr Pro Ser Pro Ser Trp Leu
 1               5                  10                  15

Lys Tyr Lys Ala Leu Xaa Xaa Xaa
            20

<210> SEQ ID NO 35
<211> LENGTH: 25
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: X is any naturally-occurring amino acid, unconventional amino acid or amino acid analog
<220> FEATURE:
<221> NAME/KEY: MISC_FEATURE
<222> LOCATION: (22)..(25)
<223> OTHER INFORMATION: X is any naturally-occurring amino acid, unconventional amino acid or amino acid analog

<400> SEQUENCE: 35

Xaa Xaa Xaa Xaa Xaa Leu Ser Ala Leu Thr Pro Ser Pro Ser Trp Leu
 1               5                  10                  15

Lys Tyr Lys Ala Leu Xaa Xaa Xaa Xaa
            20                  25

<210> SEQ ID NO 36
<211> LENGTH: 26
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: X is any naturally-occurring amino acid, unconventional amino acid or amino acid analog
<220> FEATURE:
<221> NAME/KEY: MISC_FEATURE
<222> LOCATION: (22)..(26)
<223> OTHER INFORMATION: X is any naturally-occurring amino acid, unconventional amino acid or amino acid analog

<400> SEQUENCE: 36

Xaa Xaa Xaa Xaa Xaa Leu Ser Ala Leu Thr Pro Ser Pro Ser Trp Leu
 1               5                  10                  15

Lys Tyr Lys Ala Leu Xaa Xaa Xaa Xaa Xaa
            20                  25